(12) United States Patent
Hagiwara et al.

(10) Patent No.: US 7,786,151 B2
(45) Date of Patent: Aug. 31, 2010

(54) THERAPEUTIC COMPOSITION OF TREATING ABNORMAL SPLICING CAUSED BY THE EXCESSIVE KINASE INDUCTION

(75) Inventors: Masatoshi Hagiwara, Tokyo (JP); Masaaki Suzuki, Aichi (JP)

(73) Assignee: KinoPharma, Inc., Tokyo (JP)

( * ) Notice: Subject to any disclaimer, the term of this patent is extended or adjusted under 35 U.S.C. 154(b) by 977 days.

(21) Appl. No.: 11/029,470

(22) Filed: Jan. 6, 2005

(65) Prior Publication Data

US 2005/0171026 A1    Aug. 4, 2005

Related U.S. Application Data

(60) Provisional application No. 60/534,978, filed on Jan. 9, 2004.

(51) Int. Cl.
- *A01N 43/82* (2006.01)
- *A01N 43/78* (2006.01)
- *A61K 31/425* (2006.01)

(52) U.S. Cl. .................. 514/367; 514/360; 514/365; 514/366

(58) Field of Classification Search ............... 514/23, 514/360, 365, 366, 367
See application file for complete search history.

(56) References Cited

U.S. PATENT DOCUMENTS

| | | | |
|---|---|---|---|
| 2,112,139 A | 3/1938 | Brooker et al. | |
| 2,429,469 A | 10/1947 | Keyes | |
| 2,441,342 A | 5/1948 | Anish | |
| 2,441,529 A | 5/1948 | Brooker et al. | |
| 2,468,577 A | 4/1949 | Van Dormael et al. | |

FOREIGN PATENT DOCUMENTS

| | | | |
|---|---|---|---|
| DE | 670505 | | 1/1939 |
| EP | 0 135 863 A2 | | 4/1985 |
| FR | 808598 | | 2/1937 |
| GB | 625066 | | 6/1949 |
| GB | 2081705 | * | 2/1982 |
| JP | 60-188943 A | | 9/1985 |

OTHER PUBLICATIONS

Muraki et al., "Manipulation of Alternative Splicing by a Newly Developed Inhibitor of Clks", J. Bio. Chem, vol. 279, No. 23, pp. 24246-24254, 2004.*

Taylor et al., "The infra-red spectroscopy of some highly conjugated systems", Spectrochemica Acta, vol. 33A pp. 589-599, 1977.*

Gupta et al., "Methine bases in the benzothiazole, benzoselenazole, and quinoline series, and geometry and conformational preferences of their acyl derivatives", Can. J. Chem., vol. 73, pp. 1278-1286, 1995.

Brooker et al., "Studies in the Cyanine Dye Series. XI.1. The Merocyanines", vol. 73, Journal of American Chemical Society, Communication No. 1396, p. 5326, 1951.

Bregant, "O nekim halogenom supstituiranirn karbocijaninskim bojama", Arhiv. za Kemiju (STN/CAS and CISTI), vol. 23, pp. 188-191, 1952.

Sveshnikov et al., Doklady Akademii Nauk SSSR, vol. 88, pp. 281-284, 1953.

Kiprianov et al., "Reaction of Methylene Derivatives of the Thiazole Series with Alkyl Halides", Zhurnal Obshchei Khimii (STN/CAS and CISTI), vol. 20, pp. 145-157, 1950.

Office Action issued Aug. 3, 2009 in corresponding Australian Application No. 2005200040.

* cited by examiner

*Primary Examiner*—Traviss C McIntosh, III
(74) *Attorney, Agent, or Firm*—Birch, Stewart, Kolasch & Birch, LLP

(57) ABSTRACT

The present invention provides a composition of treating, preventing abnormal splicing caused by the excessive kinase induction, which comprises TG003 and a method using the same of treating, preventing abnormal splicing caused by the excessive kinase induction.

6 Claims, 23 Drawing Sheets
(4 of 23 Drawing Sheet(s) Filed in Color)

Fig. 1A

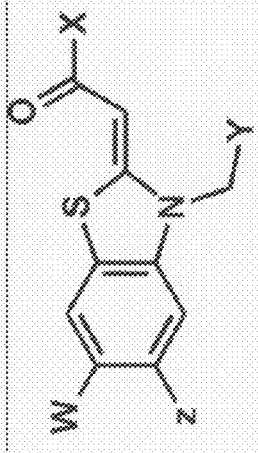

| Compounds | X | Y | Z | W | IC₅₀ mClk1 | mClk2 | mClk3 | mClk4 |
|---|---|---|---|---|---|---|---|---|
| TG001 | CH₃ | CH₃ | H | H | 2.5 µM | >10 µM | >10 µM | 1 µM |
| TG002 | CH₃ | CH₃ | CH₃ | H | 5 µM | >10 µM | >10 µM | 2 µM |
| TG003 | CH₃ | CH₃ | CH₃O | H | 20 nM | 200 nM | >10 µM | 15 nM |
| TG004 | CH₃ | CH₃ | F | H | 70 nM | 900 nM | >10 µM | 70 nM |
| TG005 | CH₃ | CH₃ | CH₃O | CH₃O | >10 µM | >10 µM | >10 µM | >10 µM |
| TG006 | CH₃ | CH₃ | C₂H₅O | H | 700 nM | 10 µM | >10 µM | 800 nM |
| TG007 | CH₃ | CH₃ | H₃C-C(O)O | H | 30 nM | 300 nM | >10 µM | 25 nM |
| TG008 | CH₃ | CH₃-C₆H₄ | CH₃O | H | 300 nM | >10 µM | >10 µM | 500 nM |
| TG009 | CH₂CH₃ | CH₃ | H | H | 8 µM | >10 µM | >10 µM | 2 µM |
| TG010 | CH₂CH₃ | CH₃ | CH₃O | H | 40 nM | 300 nM | >10 µM | 40 nM |
| TG011 | CH₂CH₃ | CH₃-C₆H₄ | CH₃O | H | 400 nM | 10 µM | >10 µM | 800 nM |
| TG012 | CH₃-C₆H₄ | CH₃ | CH₃O | H | 250 nM | >10 µM | >10 µM | 220 nM |

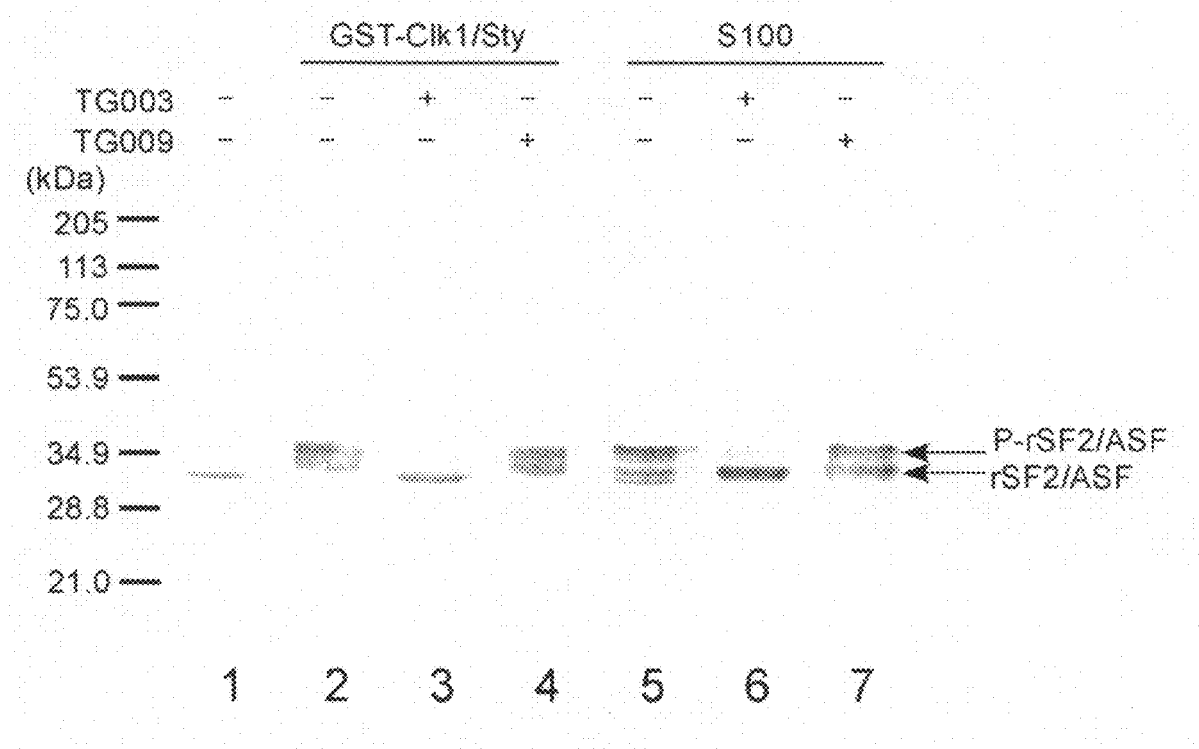

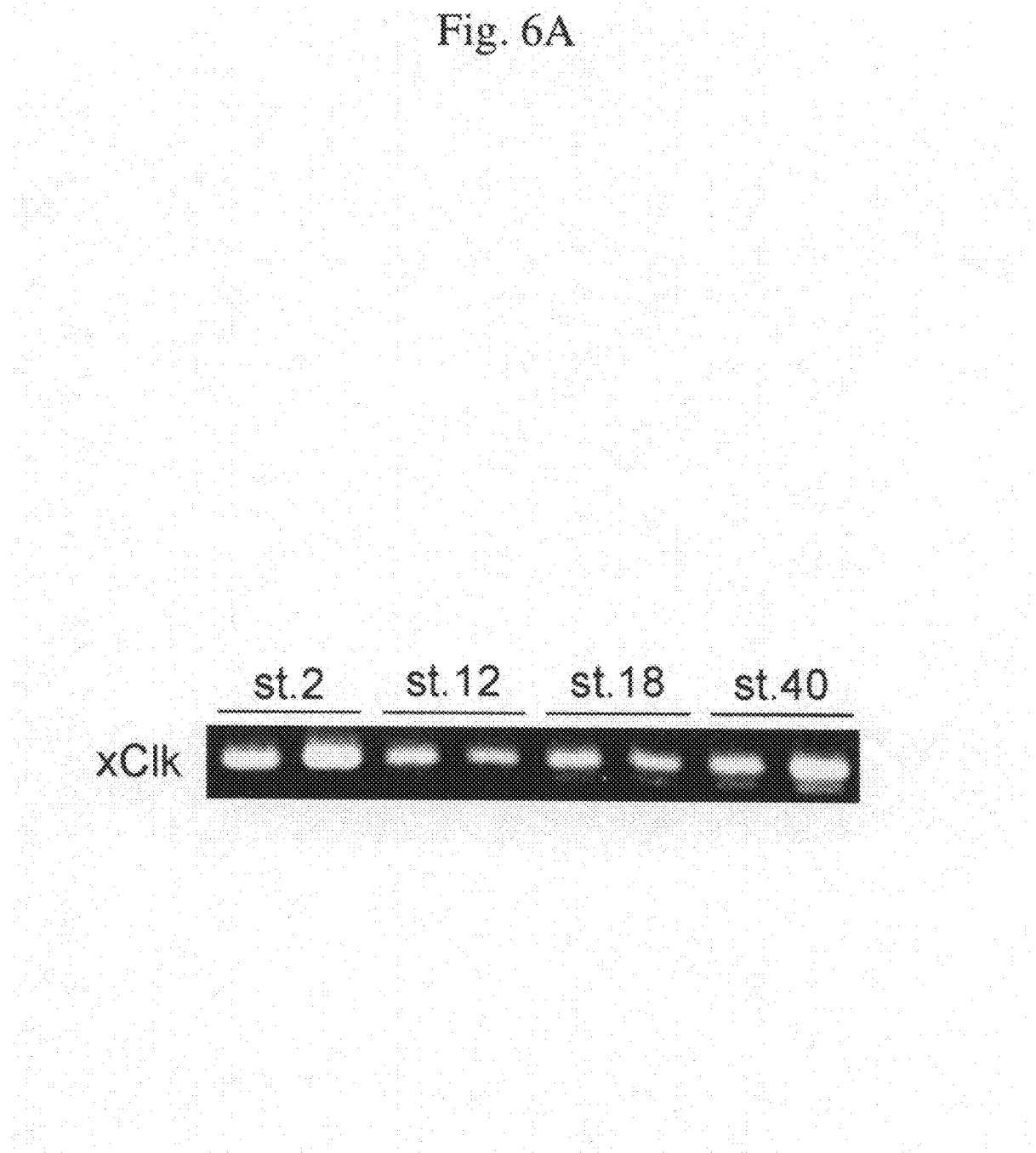

Fig. 6D

| | | Normal | Abnormal | | | | Total % (number) |
|---|---|---|---|---|---|---|---|
| | | | Ventral | | Dorsal | | |
| | | | mild | severe | mild | severe | |
| DMSO | uninjected | 87.5 (21) | | | 12.5 (3) | | 100 (24) |
| | xClk | | | | 33.3 (8) | 66.6 (16) | 100 (24) |
| 10 μM TG003 | uninjected | 81.5 (22) | 11.1 (3) | 7.4 (2) | | | 100 (27) |
| | xClk | 75.0 (18) | 25.0 (6) | | | | 100 (24) |

Fig. 8A

```
hClk2  -------WPHPRRYHSSERGSRGSYEEHVRSFKHKRRRSRSWSSSDRTRRRFEDSYHRSRSSYDRRVYDRRYC  74
mClk2  -------WPHPRRYHSSERGSRGSYHEGSYHEHQSRRKHKRRRSRSMSSSSDRTPRRRFEDSYHVRSFSSYDDHSSDRRLYDRRYC  74
xClk   ----------HSRFYGSSER------GSYFSRCHRRPRRSRSHPPRRSSSDRGREPRHMFGDGYHERSRS-YEERSSDRPAYDRRYC  70
hClk3  -------WHHCKRYRSPEP------DPYLSYRMKRRRSYSREHEGRLFYPSRREPPPRRSRSRSHDRLPYQRRYRERRDS  67
mClk3  -------WHHCKRYRSPEP------DPYLTYRMKRRRSYSREHEGRLFYPSRREPPPRRSRSHDRIPYQRFYEHRDS  67
hClk4  ------WRRHSKPTHCPDWDSP-ESWGRESYRGSHKFKRRSHSSTQEMRHCKPHHQFKESDCHYLEAFSLWEFDYRDRRYV  73
hClk4  ------WRRHSKFTHCPDWDSP-ESWGHESYSGSHKFKRRSHSSTQEMRHCRPHHQFKDSDCHYLEARCLWEFDYRDRRYI  73
mClk4  ------WRRHSKFTYCFDWDKDWDYGKMRSSSSHKRKPSHSSRKPSHSSRDDMKRPCK--YNHSKMCDSHYLESRGIMEKDYHSRRWI  73
hClk1  ------WRHSKFTYCFDWDERDWDYGTWRSSSHKRKPSHSSSRQKROR--YDHSKTIDSYLESRSIWEKAHSRRIV  73
mClk1  -----RHDTADHSPPLAEAPSPPRITNTHTRSAAKRPRHELDAKKAQISKEPTFD  80
dmDOA  MCVRFQWPRTRLHHSRDRSSAGTEDKRFRHDTADHSPPLAEAPSPPRITNTHTRSAAKRPRHELDAKKAQISKEPTFD  80 hClk2  GSYRNDYSRDRGDAYDIDYRHSYEYQRENSSYRSQRSSRRKHRRRRRRSRTFSRSSQ--HSSRRAKSVELDAEGHLI  152
mClk2  GSYRNDYSRDRGEAYDTDFRQSYEYHRENSSYRSQRSSRRKHRRRPRRSRTFSRSS--HSSRRAKSVELDAEGHLI  151
xClk   DSYRNDYSRDKGDVYNETYDYKHSRD-D----SYRSTRRKQKRRNRFTRFYQSSERSRQQSSRREAKSVEDDVEGHLV  144
hClk3  DTYRCEERSPSFGEDYGPSRSFHFRRSRERGPYRTFKHAHHCHKRRTRSCSSASSREQQ--SSKRSSREAKSVEDIKEGHLI  145
mClk3  DTYRCEERSPSFGEDCYGSSRSHFRRERAPYRTRKHAHHCHKRRTRSCSSASSREQQ--SSKRSSRSVEIDKEGHLI  145
hClk4  DEYRMDYCEGYVPRHYHRDIESGPIHQSKSSVRSRRSSPKRKR--MFHQSSHQSKSKE-HRRKRSRSIEIDEEGHLI  148
mClk4  DEYRMDYCESYVPRHFRRDVESTYRIHQSKSSVRSRGSRSSYRSKS--HRRKFSRSIEIDEEGHLI  148
hClk1  DEYRMDYTQSCEPGHRQRDHESRYQWHSSKSSGRSGRSSYRSYNSKHRSRHHTSHRRSHGKS--HRRKSVELDEEGHLI  150
mClk1  DEYRNDYMG-YEPGIPYGEPGSRYQMHSSKSGREGESSYNSKHRSRHHTSQHHSHGKS--HRRKRSVELDEEGHLI  149
dmDOA  DSISTRRKERSKRSHRKSPAASREQHKYRYRDETSHSSRRHFDRAKDERDSGENNRQS-QAKTAKPVIQDDADGHLI  159
```

Fig. 8B

| | | |
|---|---|---|
| hClk2 | YHVGDMLQERYEIVSTLIG EGTFGRVVQCV DHRRGGA RVALKIIKNVEKY KEARPLEINVLEKINEKDPDMKNICVVQFFDK | 232 |
| mClk2 | YHVGDMLQERYEIVSTLIG EGTFGRVVQCV DHPRGGTRVALKIIKNVEKY KEARPLEINVLEKINEKDPDMKNICVVQFFDK | 231 |
| xClk | YHSGDMLQERYEIVSTLIG EGTSGRVVQCK DHRRGGSRVALKIIKMVEKY KEARPLEINVLEKINEKDPENKHICVVQFFDK | 224 |
| hClk3 | CRIGDMLQERYEIVNGNLG EGTFGKVVEQL DHARGKSQVALKIIRMVGKY PEARLEINVLKIKEKDKEMKFLCVLMSPDK | 225 |
| mClk3 | CRIGDMLQERYEIVNGNLG EGTFGKVVEQL DHARGKSQVALKIIRMVGKY PEARLEINVLKIKEKDKEMKFLCVLMSPDK | 225 |
| hClk4 | CQSGDVLRARYEIVDTLIG EGAFGKVVECI DHGMDGMHKAVEIVKIVKNVGRW REARSEIQVLEHLNSTDPNSVFRCVQMLEW | 228 |
| mClk4 | CQSGDVLRARYEIVDTLIG EGAFGKVVECI DHGMDGMHKAVEIVKIVKNVGRW REARSEIQVLEHLNSTDPNSVFRCVQMLEW | 228 |
| hClk1 | CQSGDVLSARYEIVDTLIG EGAFGKVVECI DHKAGERHVAVKIVKNVDRW REARSEIQVLEHLMTDPNSTFRCVQMLEW | 230 |
| mClk1 | CQSGDVLSARYEIVDTLIG EGAFGKVVECI DHKVGGRRVAVKIVKMVDPYCEAPQS EIQVLEHLMTDPHSTFRCVQMLEW | 229 |
| dmDOA | YHTGDIEHHRYKIMPTLG EGTFGRVVKYKDMER—DYCMALKIIKMVEKYPEARLEIMSLEKIAQKDPHCDRLCVKIDKM | 238 |

| | | |
|---|---|---|
| hClk2 | FDYHGHMCISFELLGLST DEFLK LK DMMI YDPYPIHQVRHMMFQLCQAMKFLHDWKLTHTDLKPENILFVNSDYELTVYLIENK | 312 |
| mClk2 | EDYHGHMCISFELLGLST DEDELK LK DMMI YLPYPIHQVRHMMFQLCQAMKELHDWKLIHTDLKPENILFVNSDYELTVYLIENK | 311 |
| xClk | FDYHGHMCISFELLGLST DEFLK LK EMMI YFPYPIHQVRHMMAL QLCQAMKFLHDWKLIHTDLKPENILFVSSDYELRYMMEKN | 304 |
| hClk3 | FNFHGHMCIAFELLGKNT FEF LK EMMN FCPYPLPHVRHMAYQLCHRELRENFQLIHTDLKPEMILFVNSEFETLYMEHKS | 305 |
| mClk3 | FNFHGHMCIAFELLGKNT FEF LK EMNNFCPYPLPHVRHMAYQLCHLRFLRENFQLTHTDLKPEMILFVNSEFETLYMEHKS | 305 |
| hClk4 | FDHHGHVCIVFELLGLST YDFIKENSFLPFQIDHIRQAYQICQSIMFLHHKLTHTDLKPEMILFHNKYKSDYVVKYNSKMK | 308 |
| mClk4 | FDHHGHVCIVFELLGLST YDFIKENSFLPFQIDHIRQAYQICQSIMFLHHKLTHTDLKPEMILFHNKYKSDYVVKYNSKMK | 308 |
| hClk1 | FEHHGHICIVFELLGLST VDFIKENGFLPFRLDHIRKAYQICKSVNFISNKLTHTDLKPEMILFISWFLSDYTERYMPKIK | 310 |
| mClk1 | FEHRGHICTVFELLGLST VDFIKEISFLPFRMDHIRKAYQICKSVNFLYQSDYTEKYMPKMK | 309 |
| dmDOA | FDYHGHMCIVFEMLGLSV EDF IREMYEFYPLDQVRHMAYQLCYSHKFLHDMFLTHTDLKPEMILFVDSDYTSHZMHKIN | 318 |

```
hClk2   SLQHFFFRRLRAEPP----------NKLWDSSRDISF   499
mClk2   SLQHFFFRRLRAEPP----------TKLWDSSRDISF   499
xClk    SLKHFFFNPLNGDT-----------LKHWDTGFDISF   491
hClk3   SLLHFFFAGLTPEER----------SFHTSRNPSF    490
mClk3   ALLHFFFGLTPEER-----------SFHSSRNPSF    490
hClk4   SLQHFFFDLLNK                           481
mClk4   ALQHFFFDLLNRK                          481
hClk1   SLKHFFFDLLNFSI                         484
mClk1   SLKHFFNPLNHT                           483
dmDOA   SLHHFFFDRLPPHHRVGEVSNKQPLSSGSSSSRERSHSLSR  517
```

Fig. 9

Human diseases associated with changes in the relative levels of alternative spliced isoforms[1]

| Disease | Gene | Mutation | Splicing Isoforms | Change | Analyzed tissue | Refs |
|---|---|---|---|---|---|---|
| FTDP-17 | Tau | A280K | Exon10+/- | ↓ | Brain | [20-22] |
| | | IVS10+13/14/16 | | ↑ | Brain | |
| | | L284L, N296N | | | | |
| | | N279K, S305N | | | | |
| NF2 | NF2 | 1737+3 A→T | Exon 15+/- | ↓ | Fibroblasts | [46] |
| Frasier | WT1 | IVS9+4/5/6 | KTS+/- | ↓ | Gonadal tissue | [47,48] |
| Wilms tumor | WT1 | - | KTS+/- | ↑ | Tumor tissue | [49] |
| Wilms tumor | WT1 | - | Exon5+/- | ↑ | Tumor tissue | [49] |
| Breast and ovarian cancers | BRCA1 | G1604X | Exon18+/- | ↓ | Breast carcinoma cells | [16,50] |
| Breast cancer | BRCA2 | - | Exon12+/- | ↑ | Breast carcinoma cells | [51] |
| Renal, lung and urothelial cancers | CD44 | - | CD44v6-CD44v10+/- | ↑ | Tumor tissue | [52] |
| Gastric cancer | CD44 | - | CD44v5, CD44v6+/- | ↑ | Serum | [24] |
| Papillary thyroid cancer | CD44 | - | CD44v5-CD44v10+/- | ↑ | Papillary thyroid carcinomas | [53] |
| HNSCC, lung cancer | FHIT | - | Full length/variable exon skipping | ↓ | HNSCC cells, lung cancer tissues | [54,55] |
| Invasive breast cancer | MDM2 | - | Full length/variable exon skipping | ↓ | Breast carcinoma | [56] |
| Giant cell tumors of bone | MDM2 | - | Mdm2/mdm2-b | ↑ | Giant cell tumors of bone | [57] |
| Prostate cancer | FGFR-2 | - | IIIb/IIIc | ↑ | Prostate cancer cells | [58] |
| Melanoma | Bin1 | - | Exon12A+/- | ↑ | Melanoma cells | [59] |
| Prostate cancer, lymphoma, gastric carcinoma | Bcl-2 | - | Bcl-2α/β | ↑ | Prostate cancer cells, follicular lymphomas, gastric carcinoma | [23] |
| Lymphoma, breast cancer | Bcl-x | - | Bcl-xL/S | ↑ | Lymphoma cells, breast carcinoma | [23] |
| Oral and oropharyngeal cancers | Bax | - | Bax-α/ω | ↑ | Oral and oropharyngeal carcinomas | [23] |

[1]Abbreviations: CD44v5-10, variable (alternatively spliced) exons in the CD44 gene; FTDP-17, frontotemporal dementia with Parkinson linked to chromosome 17; KTS, three last codons of exon 9 (Lys-Thr-Ser); HNSCC, head and neck squamous cell carcinoma; NF2, neurofibromatosis type II.

THERAPEUTIC COMPOSITION OF TREATING ABNORMAL SPLICING CAUSED BY THE EXCESSIVE KINASE INDUCTION

CROSS-REFERENCE TO RELATED APPLICATION

This Nonprovisional application claims priority under 35 U.S.C. § 119(a) on Patent Application No. 60/534,978 filed in United States on Jan. 9, 2004, the entire contents of which are hereby incorporated by reference.

TECHNICAL FIELD OF THE INVENTION

The present invention relates to a composition or a method of treating, preventing abnormal splicing caused by the excessive kinase induction. The composition comprises a benzothiazol compound which has a potent inhibitory effect on the activity of Clk1/Sty.

BACKGROUND OF THE INVENTION

In this specification the parenthetic number indicates the reference listed below.

Recent whole genome sequence analyses revealed that a high degree of proteomic complexity is achieved with a limited number of genes. This surprising finding underscores the importance of alternative splicing, through which a single gene can generate multiple structurally and functionally distinct protein isoforms (1). Based on genome-wide analysis, 35-60% of human genes are thought to encode at least two alternatively spliced isoforms (2). The regulation of splice site usage provides a versatile mechanism for controlling gene expression and for the generation of proteome diversity, playing essential roles in many biological processes, such as embryonic development, cell growth, and apoptosis. Splicing mutations located in either intronic or exonic regions frequently cause hereditary diseases (reviewed in Refs. 3-5). More than 15% of mutations that cause genetic disease affect pre-mRNA splicing (6). Pre-mRNA splicing is also regulated in a tissue-specific or developmental stage specific manner. Indeed, the selection of splice site can be altered by numerous extracellular stimuli, including growth factors, cytokines, hormones, depolarization, osmotic shock, and UVC irradiation through synthesis, phosphorylation, and a change in localization of serine/arginine-rich (SR)[1] proteins (7).

SR proteins are a family of essential factors required for constitutive splicing of pre-mRNA (8) and play an important role in modulating alternative splicing (9). They are highly conserved in eukaryotes and are characterized by having one or two RNA-recognition motifs at the amino terminus and an RS domain at the carboxyl terminus (10, 11). RS domains consist of multiple consecutive RS/SR dipeptide repeats and differ in length among different SR proteins. Extensive phosphorylation of serines in the RS domain occurs in all SR proteins (12, 13). Although its precise physiological role is still unknown, phosphorylation of SR proteins affects their protein-protein and protein-RNA interactions (14), intracellular localization and trafficking (15, 16), and alternative splicing of pre-mRNA (17). Spliceosome assembly may be promoted by phosphorylation of SR proteins that facilitate specific protein interactions, while preventing SR proteins from binding randomly to RNA (14). Once a functional spliceosome has formed, dephosphorylation of SR proteins appears to be necessary to allow the transesterification reactions to occur (18). Therefore, the sequential phosphorylation and dephosphorylation of SR proteins may mark the transition between stages in each round of the splicing reaction. To date, several kinases have been reported to phosphorylate SR proteins, including SRPK family kinases (19, 20), hPRP4 (21), and topoisomerase I (22), and a family of kinases termed Clk (Cdc2-like kinase), or LAMMER kinases from the consensus motif, consisting of four members (Clk 1/Sty and Clk2.4) (23, 24).

Mammalian Clk family kinases contain an SR domain and are demonstrated to phosphorylate SR proteins in vitro and SF2/ASF in vivo (24). Clks are shown to be dual-specificity kinases that autophosphorylate on tyrosine, serine, and threonine residues in overexpression systems and in vitro (24-26). When overexpressed, the catalytically inactive mutant kinases localize to nuclear speckles where splicing factors are concentrated, whereas the wild-type enzymes distribute throughout the nucleus and cause speckles to dissolve (23). The overexpression of Clks also affects splicing site selection of pre-mRNA of both its own transcript and adenovirus E1A transcripts in vivo (17). These results have led us to the current model that Clk family members regulate alternative splicing by phosphorylation of SR proteins, although their signal pathways and biological functions are largely unknown in vertebrates.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 8C:
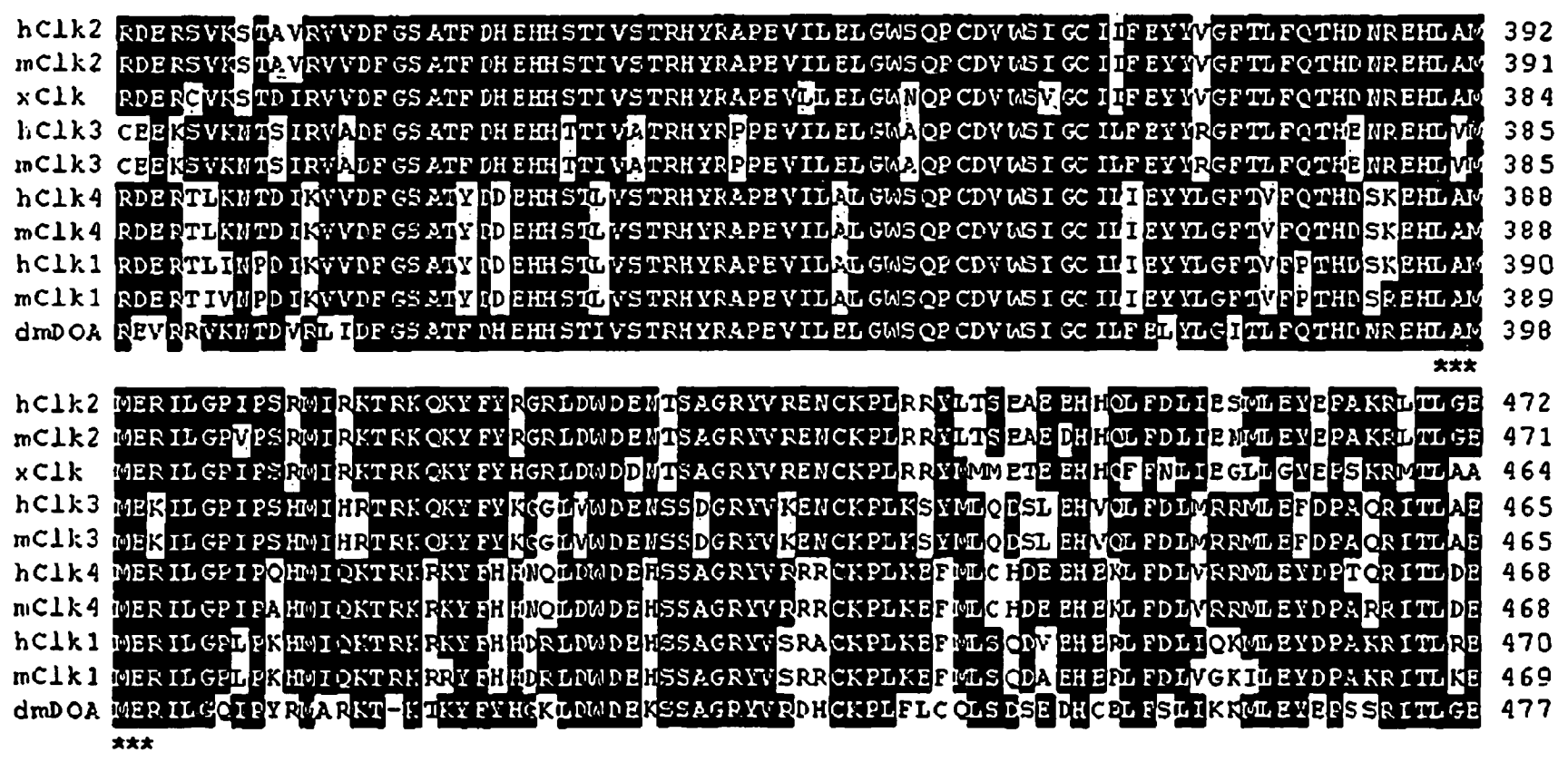

FIG. 8A-D shows an amino acid sequence alignment of Clk family. Dark shading indicates identical amino acids. To optimize homology, gaps are inserted as denoted by dash. Asterisks indicate the LAMMER motif that is characteristic to the Clk family members. Amino acid sequences of hClks, mClks and dmDOA are derived from human, mouse, and fruit fly, respectively. The GenBank accession number of each sequence is following: hClk1, BC031549; (SEQ ID NO:4); hClk2, L29218 (SEQ ID NO:5); hClk3, L29217 (SEQ ID NO:6); hClk4, AF212224 (SEQ ID NO:7); mClk1, P22518 (SEQ ID NO:8); mClk2, AF033564(SEQ ID NO:9); mClk3, AF033565 (SEQ ID NO:10); mClk4, AF033566 (SEQ ID NO:11); xClk, BC043963 (SEQ ID NO:12); dmDOA, A54099 (SEQ ID NO:13).

FIG. 9 shows diseases associated with abnormal splicing caused by the excessive kinase induction.

SUMMARY OF THE INVENTION

Figure 1B:
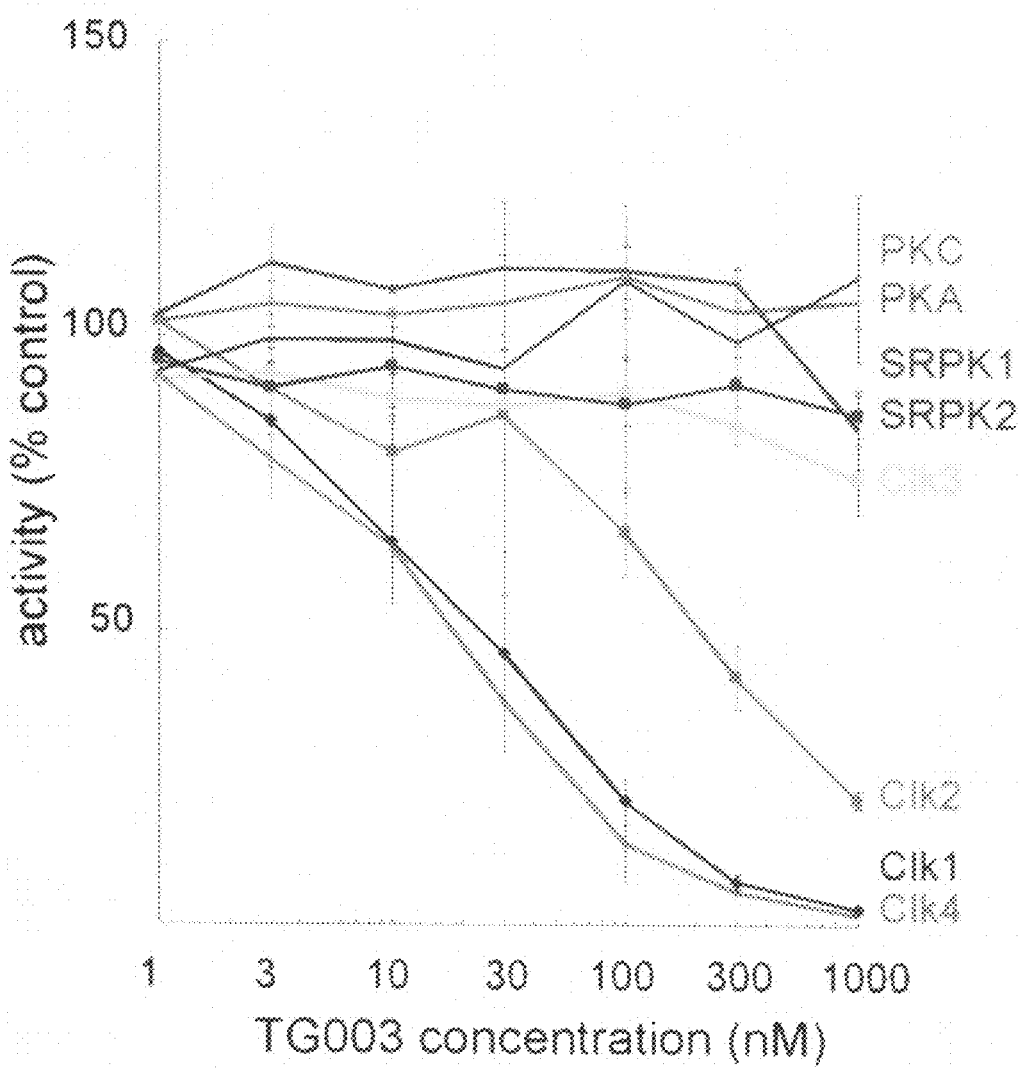
FIG. 1 shows specific inhibition of Clk1/Sty and Clk4 by TG003, a novel benzothiazole compound, in vitro. A, structure of benzothiazole derivatives and their inhibition activities for Clk family kinases. B, inhibition spectrum of TG003 for various protein kinases. The kinase and substrate were incubated ±TG003 (1-1000 nM). The average from three independent assays with the standard deviation is shown. C, double-reciprocal plots showing the competitive inhibition of ATP by TG003. Clk1/Sty kinase activity was measured at the indicated concentration of TG003 and ATP. Reciprocal velocity was plotted versus 1/[ATP]. $K_m$=3.35 µM, $V_{max}$=1.77 pmol/min/µg, and $K_i$=0.01 µM.

The abbreviations used in this specification are: SR, serine/arginine-rich; Clk, Cdc2-like kinase; PBS, phosphate-buffered saline; RT, reverse transcription; ALS, amyotrophic lateral sclerosis; EAAT2, excitatory amino acid transporters 2; SMN2, survival of motor neuron 2; DRB, 5,6-dichloro-1-β-D-ribo-furanosylbenzimidazole; HA, hemagglutinin; mAb, monoclonal antibody; nt, nucleotide.

Here we hypothesized that pharmacological inhibition of Clk kinases might provide a useful way to modulate alternative splicing, and we set out to screen a chemical library to look for compounds that affect the regulation of alternative splicing. In this paper, we report a novel compound, TG003, that inhibits the kinase activity of Clks and affects the regulation of alternative splicing mediated by phosphorylation of SR proteins in vitro and in vivo. Furthermore, TG003 also suppressed defects in early *Xenopus* development induced by excess level of Clk activity, suggesting its potential use of TG003 for manipulation of alternative splicing in vivo.

The regulation of splice site usage provides a versatile mechanism for controlling gene expression and for the generation of proteome diversity, playing an essential role in many biological processes. The importance of alternative splicing is further illustrated by the increasing number of human diseases that have been attributed to mis-splicing events. Appropriate spatial and temporal generation of splicing variants demands that alternative splicing be subjected to extensive regulation, similar to transcriptional control. The Clk (Cdc2-like kinase) family has been implicated in splicing control and consists of at least four members. Through extensive screening of a chemical library, we found that a benzothiazole compound, TG003, had a potent inhibitory effect on the activity of Clk1/Sty. TG003 inhibited SF2/ASFdependent splicing of β-globin pre-mRNA in vitro by suppression of Clk-mediated phosphorylation. This drug also suppressed serine/arginine-rich protein phosphorylation, dissociation of nuclear speckles, and Clk1/Sty-dependent alternative splicing in mammalian cells. Consistently, administration of TG003 rescued the embryonic defects induced by excessive Clk activity in *Xenopus*. Thus, TG003, a novel inhibitor of Clk family will be a valuable tool to dissect the regulatory mechanisms involving serine/arginine-rich protein phosphorylation signaling pathways in vivo, and may be applicable for the therapeutic manipulation of abnormal splicing.

The present invention is directed to a therapeutic composition of treating or preventing abnormal splicing caused by the excessive kinase induction.

The present inventors found that a benzothiazol compound such as TG003 has a potent inhibitory effect on the activity of Clk/Sty. It inhibits SF2/ASF-dependent splicing of β-globin pre-mRNA in vitro by suppression of Clk-mediated phosphorylation. Accordingly, the inventors found that a compound which has a potent inhibitory effect on the activity of Clk/Sty can be used as a therapeutic composition of treating or preventing diseases associated with abnormal splicing caused by the excessive kinase induction including FTDP-17, NF2, FRASIER, Wilms tumor, breast cancer, ovarian cancer, renal cancer, lung cancer, urothellal cancer, gastric cancer, papillary thyroid cancer, HNSCC, invasive breast cancer, glant cell tumors of bone, prostate cancer, melanoma, lymphoma, oral cancer, pharyngeal cancer and so on.

DETAILED DESCRIPTION OF THE PRESENT INVENTION

The benzothiazol compound of the present invention is represented by a general formula I.

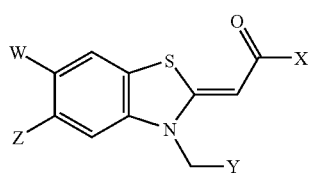

I wherein X and Y are independently linear, branched or circular hydrocarbon chain ($C_1$-$C_{10}$, preferably $C_1$-$C_3$, more preferably $C_1$), and Z and W are independently hydrogen, halogen or linear or circular carbohydrate chain ($C_1$-$C_{10}$, preferably $C_1$-$C_3$, more preferably $C_1$) which can contain hetero atoms such as oxygen. In the preferable embodiment, X and Y are independently $C_1$-$C_3$ alkyl, Z is methoxy, ethoxy, acetoxy or halogen such as F, and W is H. In the most preferable embodiment, the benzothiazol compound of the present invention is TG003, in which X and Y are $CH_3$, Z is $CH_3O$ and W is H.

The benzothiazol compound of the present invention can inhibit Clks (Cdc2-like kinase family). The $IC_{50}$ of the benzothiazol compound of the four members of Clk family is less than 50 nM, preferably less than 25 nM for Clk1/Sty, and less than 50 nM, preferably less than 20 nM for Clk4. For example, the $IC_{50}$ of TG003 is 20 nM for Clk1 and 20 nM for Clk4. The inhibition of Clk family causes Clk-mediated phosphorylation and inhibits SF2/ASF-dependent splicing of β-globin pre-mRNA. The inhibitor of Clk family also suppresses serine/arginine-rich protein phosphorylation, dissociation of nuclear speckles, and Clk1/Sty-dependent alternative splicing.

Therefore, the benzothiazol compound of the present invention can be used as a tool to dissect the regulatory mechanisms involving serine/arginine-rich protein phosphorylation signaling pathways and as a drug of treating or preventing diseases associated with abnormal splicing caused by the excessive kinase induction.

The disease associated with abnormal splicing caused by the excessive kinase induction includes FTDP-17, NF2, FRASIER, Wilms tumor, breast cancer, ovarian cancer, renal cancer, lung cancer, urothellal cancer, gastric cancer, papillary thyroid cancer, HNSCC, invasive breast cancer, glant cell tumors of bone, prostate cancer, melanoma, lymphoma, oral cancer, pharyngeal cancer, progeria, neurodegenerative diseases such as Alzheimer's disease, Parkinson's disease, amyotrophic lateral sclerosis (ALS), Huntington disease, spinocerebellar ataxia, spinal and bulbar muscular atrophy (SBMA) and epilepsy, progressive supranuclear palsy, Pick's disease, and so on. The associated genes for FTDP-17, NF2, FRASIER, Wilms tumor, breast cancer, ovarian cancer, renal cancer, lung cancer, urothellal cancer, gastric cancer, papillary thyroid cancer, HNSCC, invasive breast cancer, glant cell tumors of bone, prostate cancer, melanoma, lymphoma, oral cancer and pharyngeal cancer are shown in FIG. 9. The causative genes or proteins for neurodegenerative diseases are shown below.

| Disease | lesion area | Associated genes or proteins |
|---|---|---|
| Alzheimer's disease | cerebral cortex | Aβ, PS1, PS2, ApoE4 |
| Parkinson's disease | mesencephalon nigra | α-synuclein, UCHL-1, parkin |
| ALS | spinal cord | SOD1, ALS2CR6 |
| Huntington disease | cerebral basal nuclei | huntingtin |
| spinocerebellar ataxia | cerebellum | polyglutamine proteins, frataxin, aprataxin, α-tochopherol transfer protein |
| epilepsy | cerebral cortex | channel molecules |

The composition may include other ingredient such as a pharmacologically acceptable carrier, diluent or excipient. The pharmaceutical composition of the present invention can be administered in various forms. Examples of such an administration form include orally administration using tablets, capsules, granules, powders or syrups, or parenteral administration using injection, drop or suppository. Such a composition is produced by any known method and comprises a carrier, a diluent and an excipient, which are commonly used in the pharmaceutical field. For example, as a carrier or excipient used for a tablet, lactose, magnesium stearate or the like is used. An injection is prepared by dissolving, suspending or emulsifying the compound of the present invention or a salt thereof in a sterile aqueous or oily solution. Examples of aqueous solution used for an injection include a physiological salt solution and an isotonic solution containing glucose or another adjuvant, and the aqueous solution may be used in combination with an appropriate solution adjuvant such as alcohol, polyalcohol such as propylene glycol or a nonionic surfactant. Examples of the above-mentioned oily solution include sesame oil, soybean oil and so on, and the oily solution may be used in combination with a solution adjuvant such as benzyl benzoate or benzyl alcohol.

The dosage applied depends on symptom, age, body weight and others. In the case of oral administration, generally, it is approximately 0.001 mg to 1,000 mg per kg body weight per day, and the pharmaceutical composition with the above dosage is administered all at once, or divided several times throughout a day. In contrast, in the case of parenteral administration, 0.001 mg to 1,000 mg of the pharmaceutical composition is administered per kg body weight per day in the form of a subcutaneous injection, intramuscular injection or intravenous injection.

The present invention also provides a method of treating or preventing diseases associated with abnormal splicing caused by the excessive kinase induction. The method comprises administering the therapeutically effective amount of the compound in a patient suffering from diseases caused by abnormal splicing caused by the excessive kinase induction.

The present invention also provides an agent to study the regulatory mechanisms involving serine/arginine-rich protein phosphorylation signaling pathways in a laboratory as an inhibitor of Clks such as Clk1/Sty and Clk4.

EXAMPLE

Experimental Procedures

Synthesis of TG003

A series of benzothiazole compounds including TG003 were synthesized according to the procedures reported by Gupta et al. (27). In the case of TG003, a mixture of commercially available 5-methoxy-2-methylbenzothiazole (202 mg, 1.12 mmol) and ethyl iodide (2.70 ml, 33.7 mmol) was refluxed for 24.5 h. The precipitate was filtrated, washed with ethyl acetate (20 ml) on a funnel, and dried under reduced pressure to afford 3-ethyl-5-methoxy-2-methylbenzothiazolium iodide (270 mg, 0.805 mmol, 71.9%) as a pale green solid. To a suspension of 3-ethyl-5-methoxy-2-methylbenzothiazolium iodide (502 mg, 1.49 mmol) in acetonitrile (2.0 ml), acetic anhydride (330 µl, 3.49 mmol) and triethylamine (490 µl, 3.51 mmol) were successively added at room temperature. After refluxing for 2 h, the mixture was cooled to room temperature and concentrated under reduced pressure. Water (50 ml) was added to the residue, and the mixture was extracted with ethyl acetate (three times with 15 ml). The combined organic extracts were washed with brine (30 ml), dried over $Na_2SO_4$, filtered, and concentrated under reduced pressure. The residue was purified by silica gel column chromatography (18 g, $CH_2Cl_2$/ethyl acetate, 4:1) to afford (Z)-1-(3-ethyl-5-methoxy-2,3-dihydrobenzothiazol-2-ylidene) propan-2-one (TG003) (201 mg, 0.806 mmol, 54.1%) as a pale yellow solid.

Preparation of Recombinant Proteins

Glutathione S-transferasetagged proteins (mClk1/Sty, mClk2, mClk3, mClk4, mSRPK1, and mSRPK2) were expressed in *Escherichia coli* (DH5α or JM109) and purified as described (21). His-tagged protein (SF2/ASF) was expressed in *E. coli* BL21 (DE3) using pET32-derived vectors and purified using a nickel-nitrilotriacetic acid-agarose (Qiagen) according to the manufacturer's instructions.

In Vitro Splicing $m^7$GpppG-capped and $^{32}$P-labeled pre-mRNA substrates were made by runoff transcription of linearized human β-globin template DNA with SP6 RNA polymerase (28). HeLa cell S100 extract and purified SF2/ASF were prepared as described (29). In vitro splicing reaction mix containing the HeLa S100 extract, purified SF2/-ASF, and 20 fmol of $^{32}$P-labeled pre-mRNA was incubated with/without TG003 or TG009 at 30° C. for 3.4 h (29). The RNA products were analyzed by electrophoresis on a 5.5% polyacrylamide, 7 M urea gel and autoradiography.

In Vitro Kinase Assay

Kinase activity of Clks and SRPKs was assayed in a reaction mixture, containing 200 mM Tris-HCl (pH 7.5), 12.5 mM $MgCl_2$, 8 mM dithiothreitol, 4 mM EGTA, 1-20 µM ATP, 1 µCi of [γ-$^{32}$P]ATP, 1 µg of synthetic peptide of SF2/ASF RS domain (NH2-RSPSYGRSRSRSRSRSRSRSRSNSRSRSY-OH)(SEQ ID NO:1), and 0.1-1 µg of purified kinases in a final volume of 40 µl. cAMP-dependent protein kinase activity was assayed in a reaction mixture containing 80 mM Tris-HCl (pH 7.5), 12.5 mM $MgCl_2$, 8 mM dithiothreitol, 4 mM EGTA, 10 µM ATP, 1 µCi of [γ-$^{32}$P]ATP, 5 µg of histone H1 (Sigma), and 1 µg of catalytic subunit of rat cAMP-dependent protein kinase purified as described (30). Protein kinase C activity was assayed in a reaction mixture containing 200 mM Tris-HCl (pH 7.5), 12.5 mM $MgCl_2$, 1 mM $CaCl_2$, 80 µg/ml phosphatidylserine, 8 µg/ml diolein, 10 µM ATP, 1 µCi of [γ-$^{32}$P]ATP, 5 µg of histone H1, and 2 µl of partially purified rat protein kinase C (Seikagaku Kogyo). The final concentration of $Me_2SO$ was adjusted to 1% regardless of inhibitor concentration. The reaction mixture was incubated at 30 or 25° C. for mammalian or *Xenopus* recombinant proteins, respectively, for 10 min, and a half-portion was spotted on P81 phosphocellulose membrane (Whatman). The kinase assay conditions, including the incubation period and concentration of kinases and substrates, were optimized to maintain the linearity during incubation. The membrane was washed with 5% phosphoric acid solution (SF2/ASF RS domain) or 5% trichloroacetic solution (histone H1) at least over 15 min. The radioactivity was measured using a liquid scintillation counter. The net radioactivity was deduced by subtracting the background count from the reaction mixture without kinase, and the data are expressed as the percentage to the control sample containing the solvent.

Immunofluorescence Staining

HeLa cells grown on coverslips in a 12-well dish were transfected with Clk1/Sty expressing vectors (0.5 µg; pME-HA-mClk1/Sty or -mClk1/Sty$^{K190}$) (21) using GeneJuice (Novagen; 1.5 µl) and further incubated for 36 h. All following procedures were performed at room temperature. Cells were fixed with 4% paraformaldehyde in 250 mM Hepes-NaOH (pH 7.4) for 20 min, permeabilized with 1% Triton X-100 in PBS for 20 min, and washed four times in PBS. The cells were incubated in blocking solution (1% bovine serum albumin, 0.2% gelatin, and 0.05% Tween 20 in PBS, pH 8.0) for 30 min and incubated with rabbit anti-HA tag antibody (Santa Cruz Biotechnology; 1:1000) and mouse mAb1H4 recognizing phosphorylated SR proteins (ATCC; 1:5 of hybridoma supernatant) or mouse anti-SC35 antibody (Sigma; 1:4000) in blocking solution for 2 h. After washing several times over 1 h in PBST (PBS containing 0.05% Tween 20), the coverslips were incubated with donkey anti-mouse IgG (H+L) (Jackson Laboratories; 1:200) conjugated with Alexa 488 (Molecular Probes) and Cy3-conjugated donkey anti-rabbit IgG (H+L) (Jackson Laboratories; 1:200) in blocking solution for 2 h. After washing several times over 1 h in PBST and three times with PBS, the coverslips were mounted in Vectashield (Vector Laboratories). The images were taken using a confocal microscope (Olympus FV500 or Carl Zeiss LSM510 META). The subnuclear distribution of HA-Clk1/Sty was classified into three patterns (diffuse, intermediate, and speckle), and the number of cells showing each pattern was counted independently by four individuals for semi-quantitation.

Effects of TG003 on Cell Growth $2 \times 10^5$ HeLa cells or $1.5 \times 10^5$ COS-7 cells resuspended in 2 ml of medium were plated on 6-well dishes, and 2 µl of 10 mM TG003 dissolved in $Me_2SO$ (final concentration at 10 µM), or 2 µl of $Me_2SO$, was added to some wells. Cells were trypsinized, and the density was counted every 24 h for 3 days. Cells were then fixed with 1 ml of ice-cold 70% ethanol, washed with PBS, incubated in 1 ml of PBS containing 1 µg/ml DNase-free RNase A (Roche Applied Science) and 50 µg/ml propidium iodide (Sigma) for 20 min at 37° C., and proceeded to cell cycle analysis by FACSCalibur (BD Biosciences).

In Vivo Splicing Assay

Figure 4A:
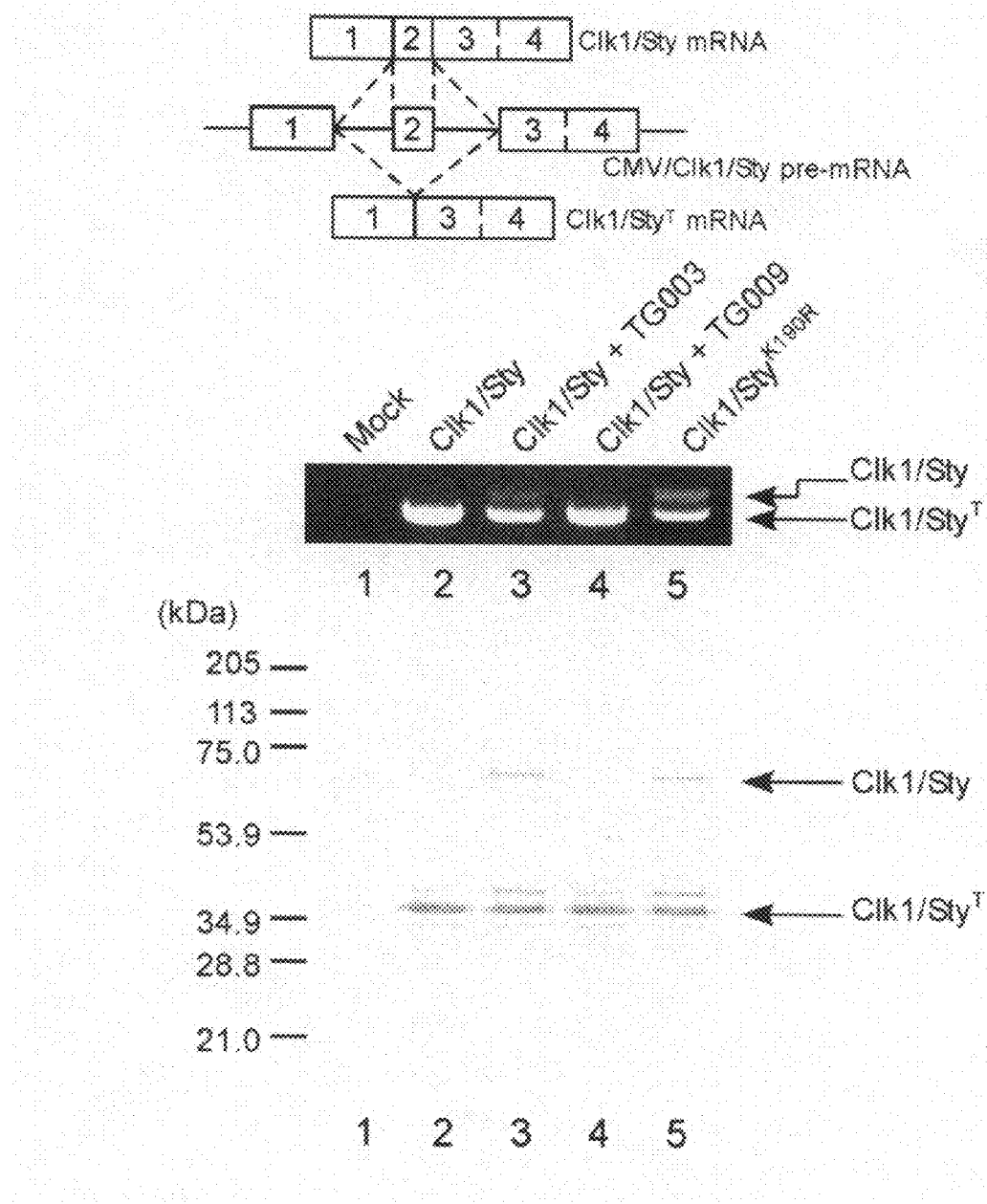
FIG. 4 shows effect of TG003 pre-mRNA alternative splicing in vivo. A, effect of TG003 on Clk1/Sty pre-mRNA alternative splicing. COS-7 cells were transfected with the expression vector (17) of Myctagged Clk1/Sty minigene (lanes 2-4), Clk/Sty$^{K190R}$ (lane 5), or an empty vector (mock; lane 1). Three hours after transfection, 10 μM TG003 (lane 3) or TG009 (lane 4) was added, and cells were further incubated for 21 h. The splicing pattern (top) was analyzed by RT-PCR (middle) and Western blotting (bottom). B, effect of TG003 on adenovirus E1A pre-mRNA alternative splicing. COS-7 cells were cotransfected with adenovirus E1A minigene construct and the expression vector of Clk1/Sty (lanes 2 and 5), Clk1/Sty$^{K190R}$ (lanes 3 and 6), or an empty vector (lanes 1 and 4). Top, diagram of the E1A mRNAs generated by alternative 5' splice site selection and a primer set used for RT-PCR (31). Bottom, RT-PCR. The position of different spliced products is indicated.

COS-7 cells grown in a 60-mm dish were transfected with Myc-tagged Clk minigene (CMV-Clk1 or -Clk1$^{K190R}$ (17); FIG. 4A) or adenovirus E1A minigene (PMT-E1A) (31) in combination with the Clk expression vector (FIG. 4B), using LipofectAMINE (Invitrogen) according to the manufacturer's instructions. Twenty four hours after transfection, the total RNA was extracted using ISOGEN (Nippon Gene); for FIG. 4A, cells were also lysed in SDS-gel loading buffer (0.1 M Tris-HCl (pH 6.8), 0.2 M dithiothreitol, 4% SDS, 20% glycerol) to prepare total cellular protein extract. Five micrograms of RNA was used for reverse transcription (RT), and then 1:50 was used for PCR amplification (94° C. for 5 min, (94° C. for 30 s, 57° C. for 30 s, and 72° C. for 1 min)×25 cycles, 72° C. for 5 min). PCR conditions, including the number of cycles and template concentrations, were optimized to maintain the linearity during amplification. PCR products were separated in agarose gel and stained with ethidium bromide. Total protein was separated in SDS-PAGE and transferred to PVDF membrane. To detect Myc-tagged Clk protein (31), the membrane was incubated with mouse anti-Myc tag antibody (MBL, Co., LTD, Nagoya, Japan) followed by alkaline phosphatase-conjugated anti-mouse IgG+A+M (H+L) (Bio-Rad). For splicing assay for endogenous genes in FIG. 5, mouse embryonic fibroblasts (STO cells) were incubated in the presence or absence of 10 µM TG003 for 4 h, and total RNA was extracted using TRIzol (Invitrogen) before RT-PCR using primers for SC35 and Clk1/Sty designed as per Pilch et al. (32). The PCR conditions were as follows: 94° C. for 5 min (94° C. for 15 s, 55° C. for 30 s, and 68° C. for 1 min)×25 cycles (SC35) or 30 cycles (Clk1/Sty).

Isolation and Sequence Analysis of *Xenopus* Clk

The total mRNA was extracted from *Xenopus* embryos at stage 2, 12, 18, and 40 using TRIzol (Invitrogen) according to the manufacturer's instruction. cDNA encoding *Xenopus* Clk was amplified by RT-PCR using SuperScriptII (Invitrogen; 42° C. for 30 min) and High Fidelity PCR Master (Roche Applied Science; 95° C. for 5 min (94° C. for 30 s, 55° C. for 30 s, 68° C. for 2 min)×25 cycles, 72° C. for 10 min) with primers designed according to the IMAGE clone of xClk (BC043963; 5'-ATGCCTCACTCCAGACGTTACGGT-TCGTCA-3' (SEQ ID NO:2) for the 5' primer and 5'-TCATCGGCTTATGTCCCGGCCAGTGTCCCA-3' (SEQ ID NO:3) for the 3' primer). The PCR products were cloned into pGEM-T Easy (Promega), and the nucleotide sequence was verified. To make the mRNA expression vector, the resulting plasmid (i.e. pGEM-T Easy containing xClk) was digested with NotI, blunted with Klenow enzyme, digested with SpeI, and ligated into pCS2+ (33) digested with XbaI and StuI. For bacterial expression, the pGEM-T Easy containing xClk was digested with NotI and inserted into NotI digested pGEX-5X-3 (Amersham Biosciences).

*Xenopus* Embryo Manipulation

*Xenopus laevis* embryos were obtained from in vitro fertilization of eggs with testes homogenates as described (34), dejellied with 3% cysteine, and washed several times with water. Embryos were staged according to Nieuwkoop and Faber (35). Embryos were cultured at 22° C. for 2 or 5 days with TG003 or its solvent ($Me_2SO$) in dark.

Microinjection of Synthetic mRNA

Capped mRNA was synthesized from linearized xClk/ CS2+vectors using the mMessage Machine kit (Ambion). Synthesized mRNA was injected into the dorsal blastomeres of four-cell stage embryos, which were further cultured in Steinberg's buffer containing 3% Ficoll with TG003 or $Me_2SO$ for 2 or 5 days, and phenotypes were scored on the 2nd day.

Results

TG003 Inhibits Clk1/Sty and Clk4 In Vitro

Figure 1C:
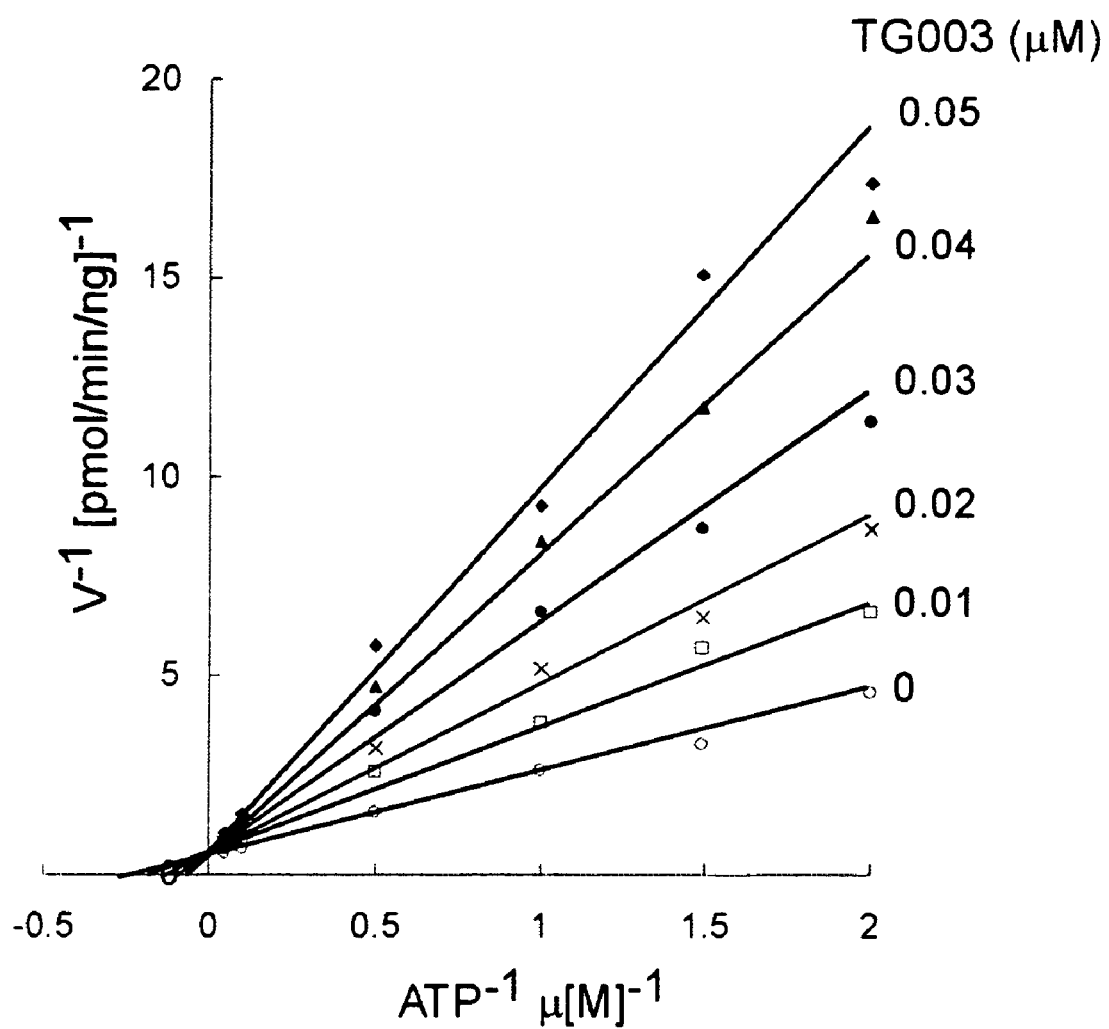

Through extensive screening of 100,000 chemical compounds in a chemical library by in vitro phosphorylation assay, we found that a benzothiazole compound had a potent inhibitory effect on the activity of Clk1/Sty. We therefore synthesized a series of benzothiazole derivatives, as shown in FIG. 1A. Among these compounds, (Z)-1-(3-ethyl-5-methoxy-2,3-dihydrobenzothiazol-2-ylidene)propan-2-one, designated TG003, showed the most potent effect on Clk1/Sty and Clk4 (IC50, 15-20 nM) and lesser on Clk2 (200 nM) (FIG. 1B). This result is consistent with the amino acid sequence similarity; Clk1/Sty and Clk4 are more closely related to each other (69% identity) than to Clk2 or Clk3 (43% identity) (24). No inhibitory effect was observed on Clk3, SRPK1, SRPK2, cAMP-dependent protein kinase, or protein kinase C up to 1 µM. The double-reciprocal Lineweaver-Burk plot indicated that TG003 acts on Clk1/Sty competitively with ATP (Km 3.35 µM) with a Ki value of 0.01 µM (FIG. 1C). TG009 is a structurally analogous compound with 500-1000 times weaker effect on Clk1/Sty and Clk4 and was used as a negative control throughout the following experiments.

TG003 Inhibits SF2/ASF— and Clk-dependent Splicing In Vitro

Because phosphorylation of SR proteins is known to be the critical regulatory step for alternative splicing (14, 36), we tested if TG003 can block the phosphorylation of recombinant His-tagged SF2/ASF (rSF2/ASF) by HeLa cytosolic S100 extract (29) or Clk1/Sty. SR proteins are phosphorylated at multiple serine residues within their RS domains, and the electrophoretic mobility of SF2/ASF and SC35, well known SR proteins, on SDS-PAGE is affected by their phosphorylation state (14, 37); phosphorylated protein shows more reduced mobility shift than unphosphorylated proteins. rSF2/ASF purified from *E. coli* is thought to be unphosphorylated. rSF2/ASF was incubated with HeLa cytosolic S100 extract (29) or Clk1/Sty as the kinase source in the splicing condition in the absence or presence of TG003 or its negative control TG009. rSF2/ASF exhibited reduced electrophoretic mobility in the presence of Clk 1/Sty (FIG. 2A, lane 2) compared with the rSF2/ASF alone (FIG. 2A, lane 1), and TG003 (1 µM) completely blocked the mobility shift (FIG. 2A, lane 3), whereas TG009 had no effect (FIG. 2A, lane 4). TG003 blocked the mobility shift of rSF2/ASF induced by S100 (FIG. 2A, lane 6), whereas TG009 again had no effect. Considering the inhibition spectrum of TG003, this result suggests that the major SR protein kinase activity in the HeLa S100 extract is either Clk1/Sty or Clk4.

Figure 2B:
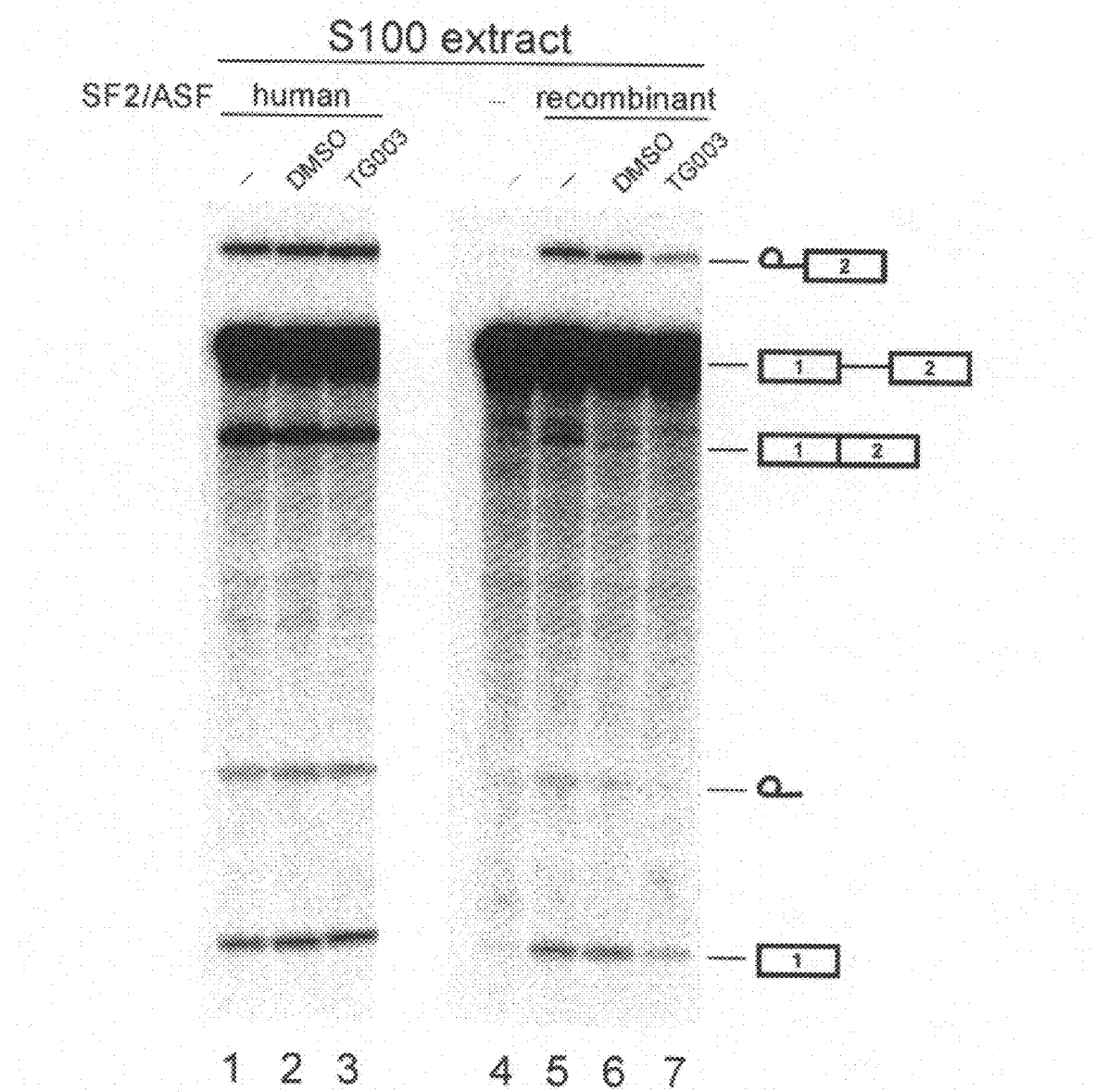
FIG. 2 shows that TG003 inhibits SF2/ASF-dependent splicing in vitro by suppression of Clk1/Sty-mediated phosphorylation. A, phosphorylation of SF2/ASF was inhibited by TG003 in HeLa cytosolic S100 extract. Recombinant SF2/ASF (rSF2/ASF; 0.2 µg) in splicing buffer was incubated for 4 h at 30° C. with either recombinant Clk1/Sty (0.5 µg) (lanes 2-4) or HeLa S100 extract (lanes 4-7) in the absence (lanes 2 and 5) or presence of 1 µM TG003 (lanes 3 and 6) or TG009 (lanes 4 and 7). Aliquots were fractionated by SDS-PAGE and analyzed by Western blotting with monoclonal antibody AK103 (37). Positions of phosphorylated and unphosphorylated rSF2/ASF are indicated on the right of the panel as P-rSF2/ASF and rSF2/ASF, respectively. Without any kinase sources, mobility of SF2/ASF is not changed during the incubation (lane 1). B, TG003 altered the pattern of the SF2/ASF dependent splicing of human β-globin in vitro. m7GpppG-capped and 32P-labeled human β-globin pre-mRNA was incubated with cytosolic S100 extract complemented with SF2/ASF purified from HeLa cells (lanes 1-3) or recombinant SF2/ASF (lanes 5-7). The solvent (DMSO) (lanes 2 and 6) or TG003 (1 µM) (lanes 3 and 7) was added to reaction mixtures before starting splicing reaction. The RNA products were analyzed by electrophoresis on a 5.5% polyacrylamide, 7 M urea gel and autoradiography. Positions of the pre-mRNA, spliced product, and intermediates are depicted by symbols on the right.

We next examined if TG003 has an effect on splicing reaction in vitro by complementation assay. Human β-globin pre-mRNA was incubated in HeLa S100 extract (29) and supplemented with either human SF2/ASF (hSF2/ASF) purified from HeLa cells or rSF2/ASF (FIG. 2B). As expected, TG003 attenuated the splicing of β-globin pre-mRNA in S100 extract complemented with rSF2/ASF (FIG. 2A, lane 7); in contrast, it had no effect when complemented with hSF2/ASF (FIG. 2A, lane 3). It is likely that the unphosphorylated rSF2/ASF needs to become phosphorylated during the incubation to support splicing reaction, which was inhibited by TG003, whereas hSF2/ASF is already phosphorylated when it was purified from HeLa cells (37). As an ATP-regenerating system and magnesium are usually used in splicing assays, SR proteins should be maintained in a phosphorylated state throughout the splicing reaction, as long as the extract contains the kinase activity and protein phosphatases are not in excess. Indeed, at the end of the splicing reaction, the majority of rSF2/ASF displayed reduced electrophoretic mobility (FIG. 2A, lane 5).

TG003 Inhibits Clk1/Sty Kinase Activity in Mammalian Cells

Figure 3A:
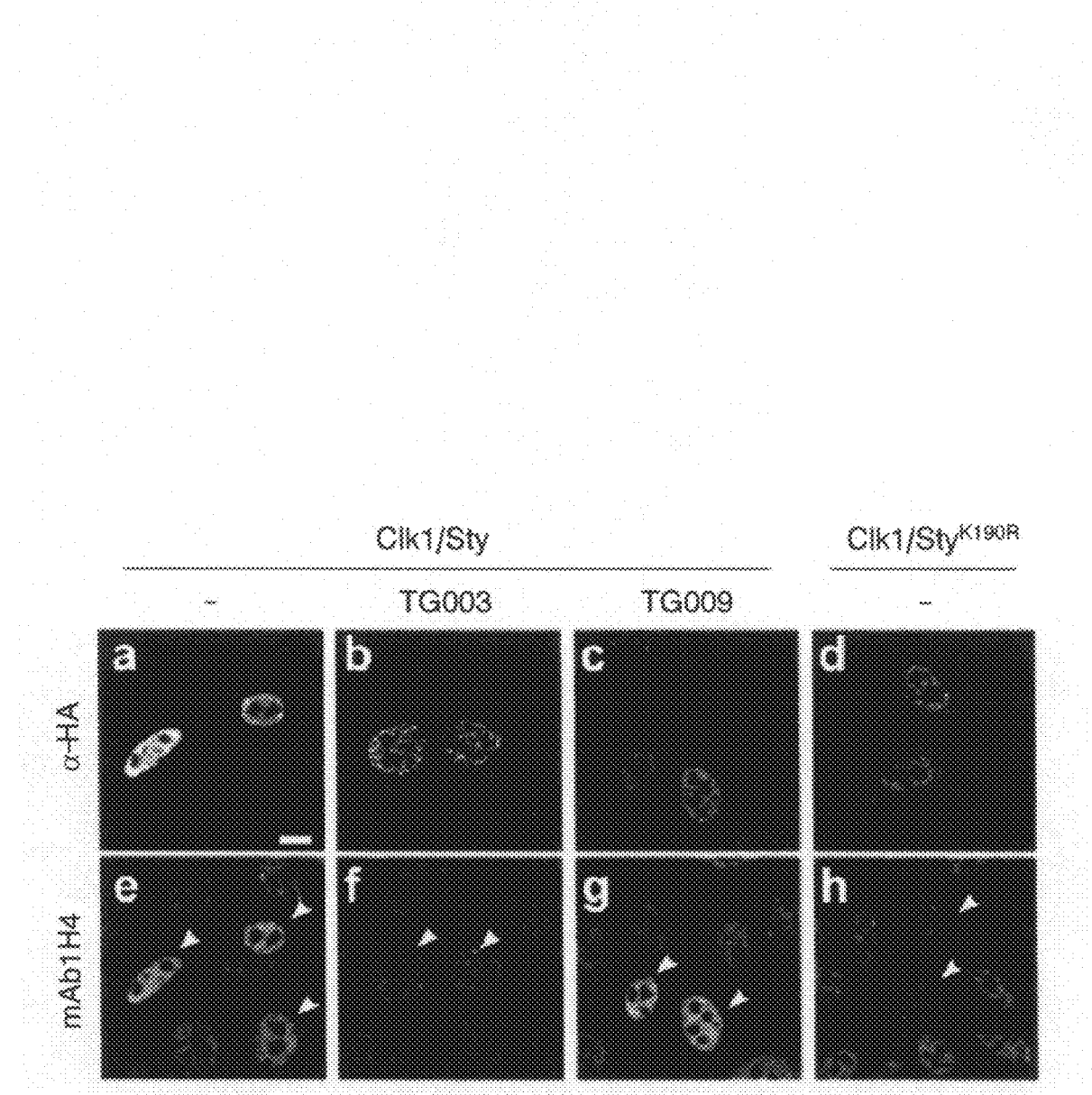
FIG. 3 shows that TG003 affects Clk kinase activity in tissue culture cells. A, TG003 suppressed hyperphosphorylation of SR proteins by Clk1/Sty. HA-tagged Clk1/Sty or Clk1/Sty$^{K190R}$ expression vector was transfected in HeLa cells, and cells were cultured for 12 h with Me$_2$SO (panels a, d, e, and h), TG003 (panels b and f), or TG009 (panels c and g) before fixation. Cells were double-stained with anti-HA antibody and anti-phospho SR proteins (mAb1H4). Arrowheads indicate the transfected cells. Bar, 10 μm. B, Western blotting. COS-7 cells were transfected and incubated as in A. Total proteins were separated in 8% polyacrylamide gel, transferred to a nitrocellulose membrane, and probed with anti-phospho SR proteins (mAb104). C, Clk kinase activity is restored after removal of TG003. HeLa cells were transfected with HA-tagged Clk1/Sty expression vector. Twenty four hours later, TG003 was added (final 10 μM) except a control sample (panels a and e), and cells were further incubated for 12 h. Cells were washed and incubated in fresh medium for 0 (panels b and f), 1 (c and g), or 2 h (d and h) before fixation. The fixed cells were stained with rabbit anti-HA (panels a-d) and mouse antiphospho SR proteins (mAb1H4; panels e-h), followed by Alexa 488-conjugated donkey anti-mouse IgG (H+L) and Cy3-conjugated donkey anti-rabbit IgG (H+L). Arrowheads indicate the transfected cells. Bar, 10 μm. The pattern of Clk1/Sty localization was categorized as speckle, diffuse, and intermediate, and the number of cells showing each pattern was counted at each time point (n>32) by four individuals. The percentage with standard deviation is expressed as bar graph.
Figure 3B:
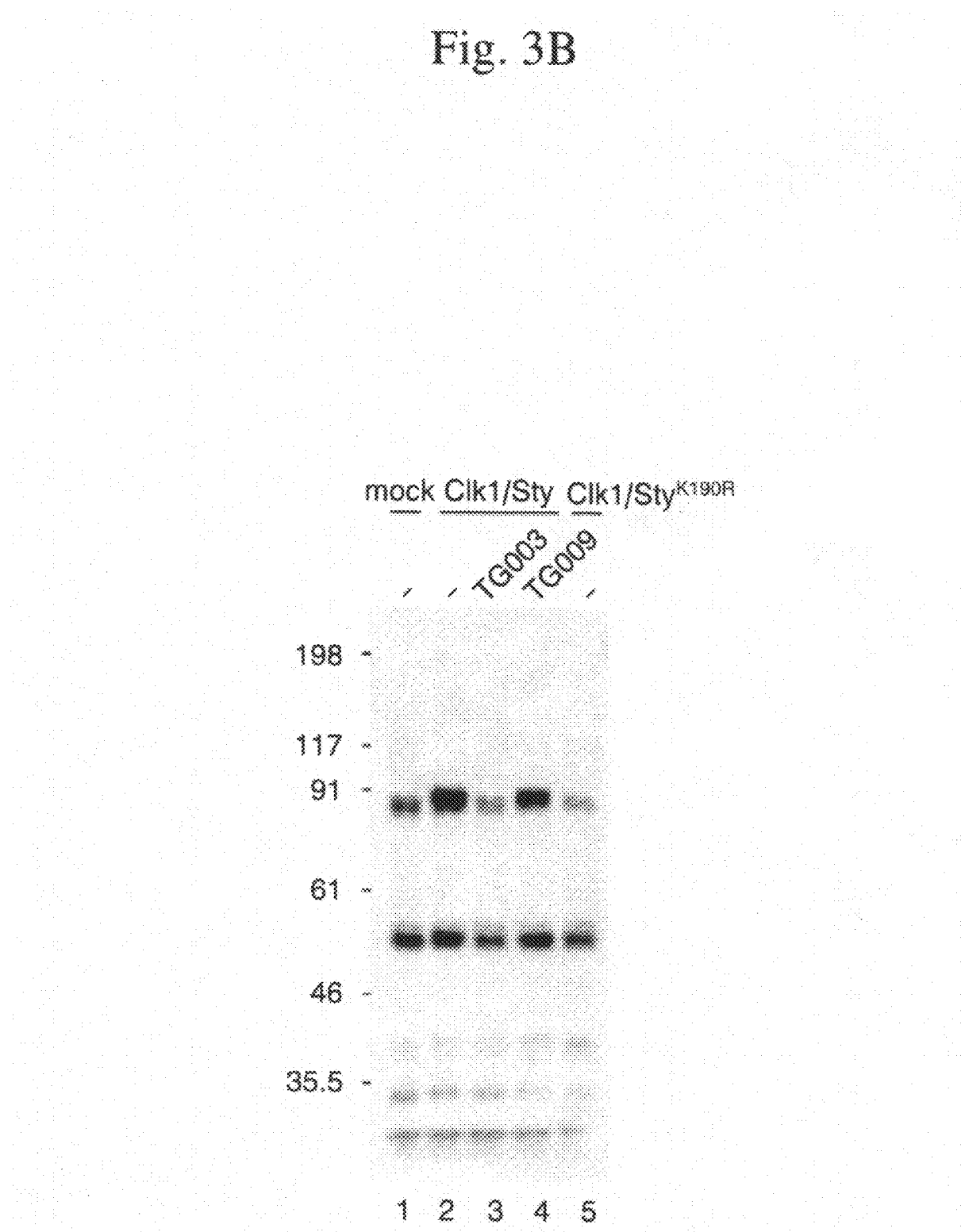

Many splicing factors including small nuclear ribonucleoproteins and SR proteins are found to be localized in nuclear structures termed speckles, proposed to act as storage/assembly/modification sites for splicing components (reviewed in Ref. 38). Overexpression of Clk kinases can modulate the subnuclear localization of SR proteins and Clk itself from speckles to nucleoplasm (17, 23), suggesting that Clk kinase phosphorylates SR proteins and Clk itself to promote their release from storage sites and increases its effective nucleoplasmic concentration and availability to participate in the splicing reaction (17). To address whether TG003 can inhibit the kinase activity of Clk1/Sty in living cells, we first assessed if the compound inhibits the hyperphosphorylation of SR proteins and its redistribution from speckles to a diffuse nucleoplasmic pattern induced by overexpression of HA-tagged Clk1/Sty. Even in the presence of the negative control drug TG009 (10 μM), transfected wild-type HA-Clk1/Sty caused a redistribution of splicing factor SC35 (not shown) and of Clk1/Sty itself from a speckled to a diffuse pattern with enhanced staining by mAb1H4, which specifically recognizes phosphorylated SR proteins (39) (FIG. 3A, panels a, c, e, and g). When we administered 10 μM TG003 into the culture media, HA-Clk1/Sty was localized in nuclear speckles in HA-Clk1/Sty-overexpressing HeLa cells with suppressed phosphorylation of SR proteins (FIG. 3A, panels b and f), as observed in cells expressing catalytically inactive HA-Clk 1/Sty (Clk1/Sty$^{K190R}$) (FIG. 3A, panels d and h). The inhibition of Clk1/Sty-induced phosphorylation by TG003 was further supported by Western blotting analysis (FIG. 3B). COS-7 cells were transfected with HA-Clk1/Sty, HA-Clk1/Sty$^{K109R}$, or mock vector as above and incubated in the absence or presence of 10 μM TG003 or TG009 for 12 h. Total cellular protein was prepared, fractionated in 8% SDS-polyacrylamide gel, and immunoblotted with mAb104, which also recognizes phospho-SR proteins (40) (FIG. 3B) or mAb1H4 (not shown). When wild-type Clk1/Sty was overexpressed, the band at ~75 kDa showed reduced mobility with increased intensity (FIG. 3B, lane 2), compared with mock or Clk1/StyK R-transfected cells (FIG. 3B, controls, lanes 1 and 5), suggesting hyperphosphorylation of SRp75 by Clk1/Sty. Administration of TG003, but not TG009, inhibited such effect in Clk1/Sty-overexpressed cells (FIG. 3B, lanes 3 and 4). These data imply that TG003 penetrates into cells and inhibits the kinase activity of Clks in vivo.

Figure 3C:
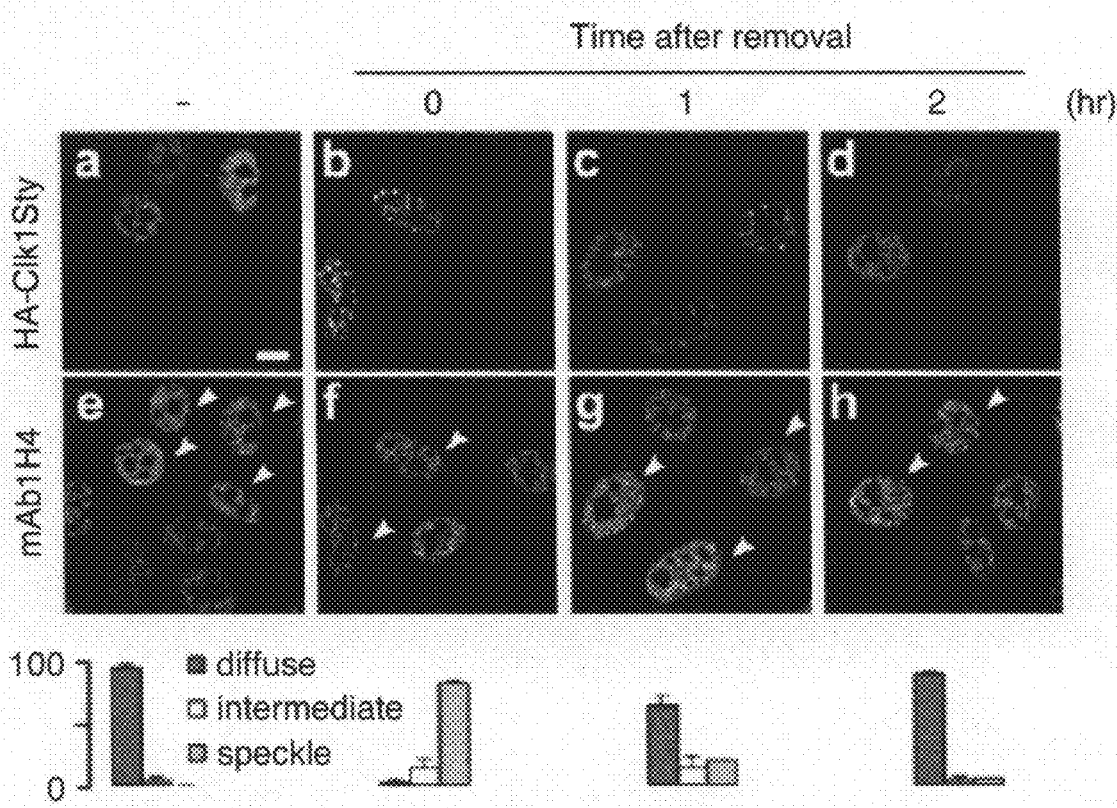

To analyze if the TG003 effect is reversible, HeLa cells transfected with HA-Clk1/Sty expression vector were incubated for 12 h with TG003 and then washed and further incubated in fresh medium (FIG. 3C). After the release from TG003 administration, the distribution of HA-Clk1/Sty became diffuse in most cells in 1 h (FIG. 3C, panel c) and almost all cells in 2 h (FIG. 3C, panel d). The level of SR phosphorylation in HA-Clk1/Sty-positive cells also increased in 2 h (FIG. 3C, panels g and h). Thus, the inhibitory effects of the drug on SR protein phosphorylation and relocalization appeared to be reversible. It should be noted that TG003 appears to have no toxic effect on growth of HeLa and COS-7 cells at 10 μM concentration for a few days, because the growth rate and cell cycle profile of TG003-treated and -untreated cells were similar (Supplemental Material FIG. 1).

TG003 Alters Clk1 Sty-regulated Alternative Splicing In Vivo

Figure 4B:
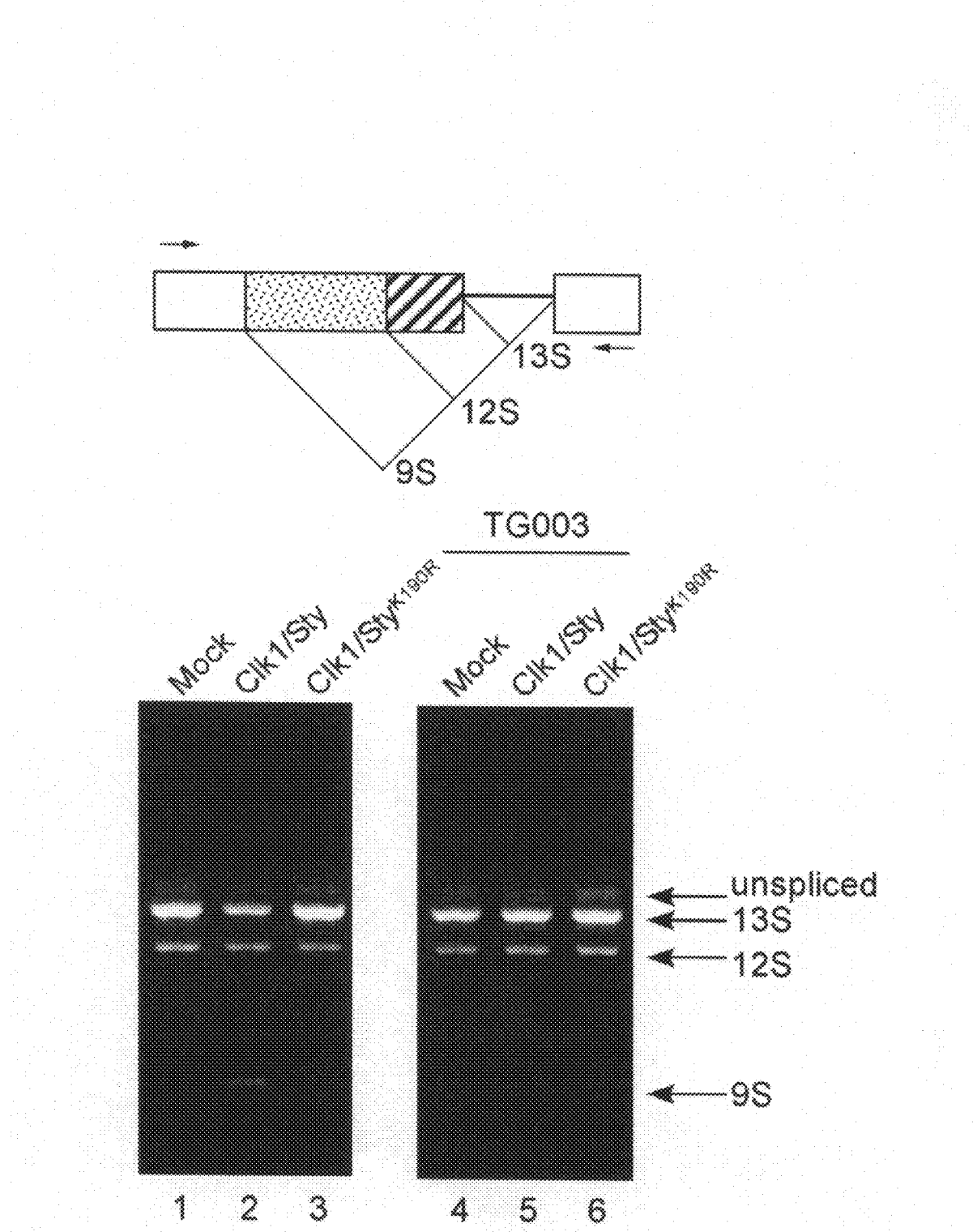

We next tested if TG003 affects Clk1/Sty-regulated alternative splicing in vivo. Mouse Clk1/Sty isoforms are translated from two alternatively spliced transcripts encoding either a full-length catalytically active protein (Clk1/Sty) or a truncated protein lacking the catalytic domain (Clk1/Sty$^T$) (17) (FIG. 4A, upper panel). It is reported that Clk1/Sty regulates splicing of its own pre-mRNA according to its kinase activity; increased expression of the catalytically active Clk1/Sty influences splicing to generate the splicing variant that lacks exon 2 and thus encodes the kinase-negative Clk1/Sty$^T$. We assessed the effect of the compound on the kinase activity-mediated exon skipping of Clk1/Sty pre-mRNA by RT-PCR and Western blotting. As shown in FIG. 4A, TG003 suppressed the exon skipping and increased the levels of full-length form (FIG. 4A, lane 3), as observed in cells transfected with the kinase-negative one (FIG. 4A, lane 5). The effect of TG003 on a different type of alternative splicing was further tested (FIG. 4B). The adenovirus E1A pre-mRNA is spliced into three predominant mRNA variants termed 13 S, 12 S, and 9 S mRNAs, through the use of three alternative 5' splice sites and a single 3' splice site (41). COS-7 cells were transfected with a reporter adenovirus E1A gene (31). Co-transfection of Clk1/Sty increased the use of the most distal 5' splice site, which gives rise to the 9 S isoforms (31) (FIG. 4B, lane 2). TG003 also inhibited the production of the 9 S isoform (FIG. 4B, lane 5). Thus, the alteration of splicing site selection induced by Clk kinase activity was suppressed by TG003 in mammalian cells.

TG003 Affects the Alternative Splicing of Endogenous Genes

Figure 5A:
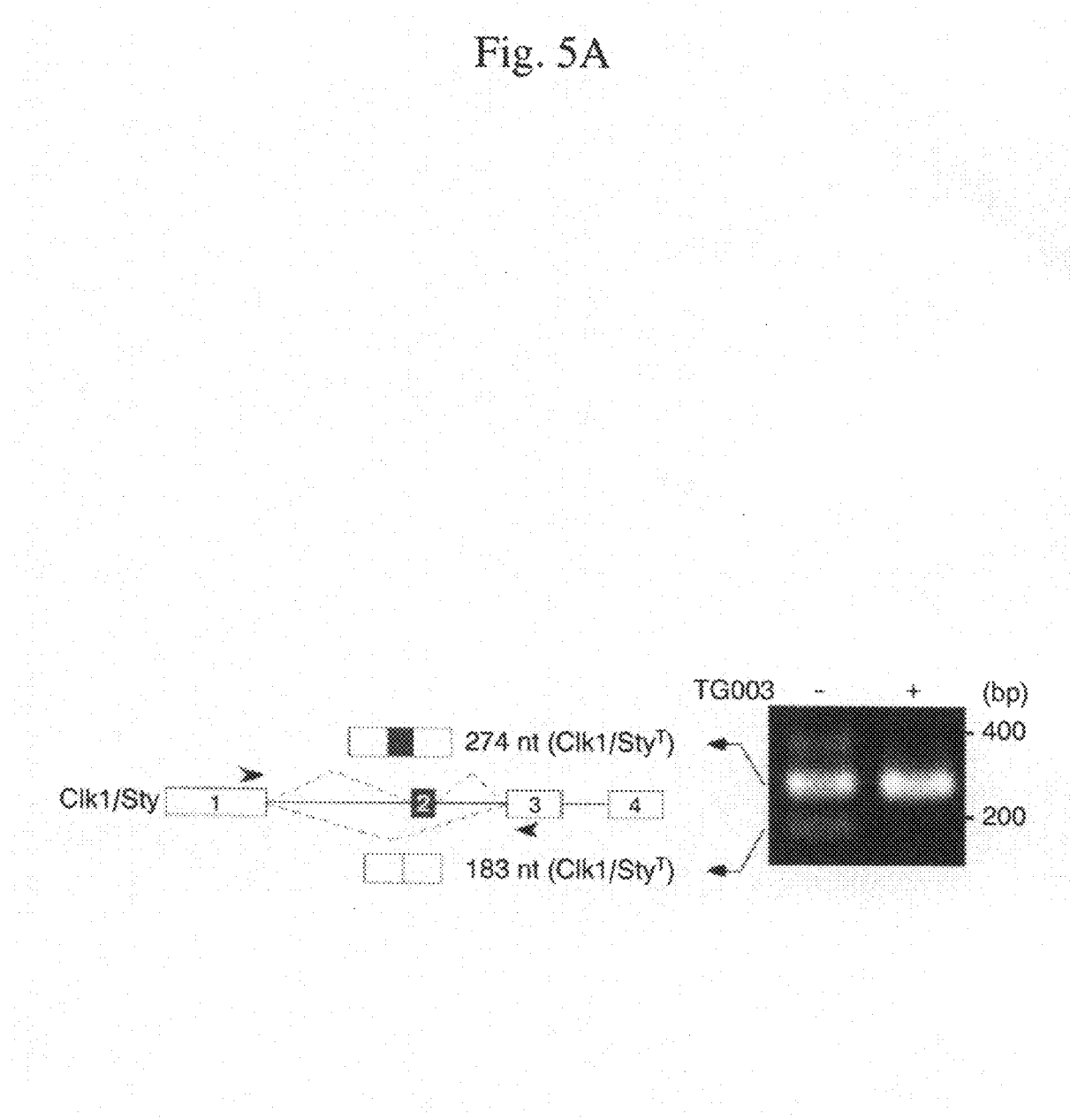
FIG. 5 shows that treatment with TG003 changes the splicing pattern of endogenous SC35 and Clk1/Sty mRNAs. Mouse STO cells were incubated ±10 μM TG003 for 4 h. Total RNA was purified, and the splicing pattern of Clk1/Sty and SC35 was analyzed by RT-PCR. The splicing variants and their expected PCR products using the primers indicated by arrowheads are illustrated on the left. A, effect of TG003 on Clk1/Sty alternative splicing. The 183-bp band corresponding to Clk1/Sty$^T$ disappears in TG003. B, effect of TG003 on SC35 alternative splicing. The intensity ratio of three bands is changed in TG003.
Figure 5B:
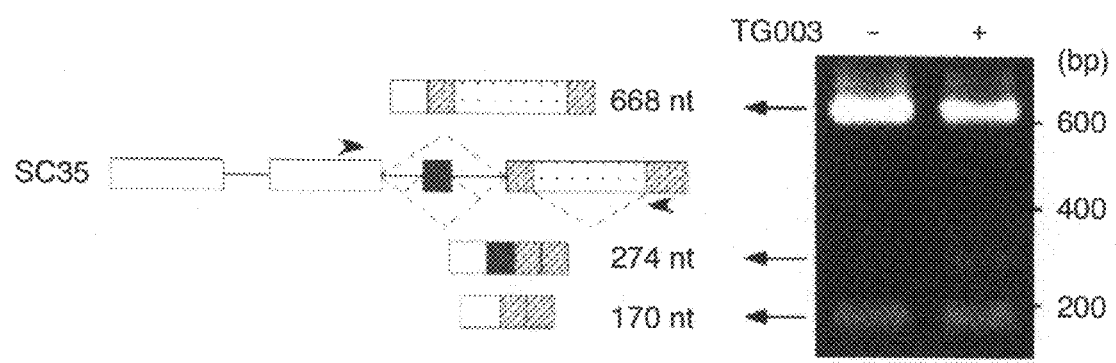

We wondered whether TG003 induces changes in the splicing profile of endogenous genes, and we analyzed those of Clk1/Sty and SC35, because the alteration of splicing pattern of these genes by drug treatment has been reported (32, 42). Among several mouse cell lines tested, RT-PCR revealed that immortal embryonic fibroblasts (STO cells) showed changes in splicing profiles of both genes by administration of 10 μM TG003 for 4 h (FIG. 5). In untreated cells, PCR product corresponding to the short form (183 nt), which produces kinasenegative Clk1/Sty$^T$, was observed in addition to the long form (274 nt) producing the full-length (kinase-positive) Clk1/Sty (FIG. 5A). This short form disappeared when cells were administered TG003, in good agreement with the feedback regulation of Clk expression (17) (FIG. 4A). The subtle change of SC35 splicing profile was also observed (FIG. 5B). In untreated cells, PCR products corresponding to the major (668 nt) and the minor (170 and 274 nt) transcripts for SC35 were detected. TG003 treatment increased the band intensity of 274 nt and decreased that of 668 nt. These results indicate that alternative splicing of endogenous genes could be controlled by TG003.

TG003 Suppresses Developmental Abnormality Induced by xClk

Figure 6B:
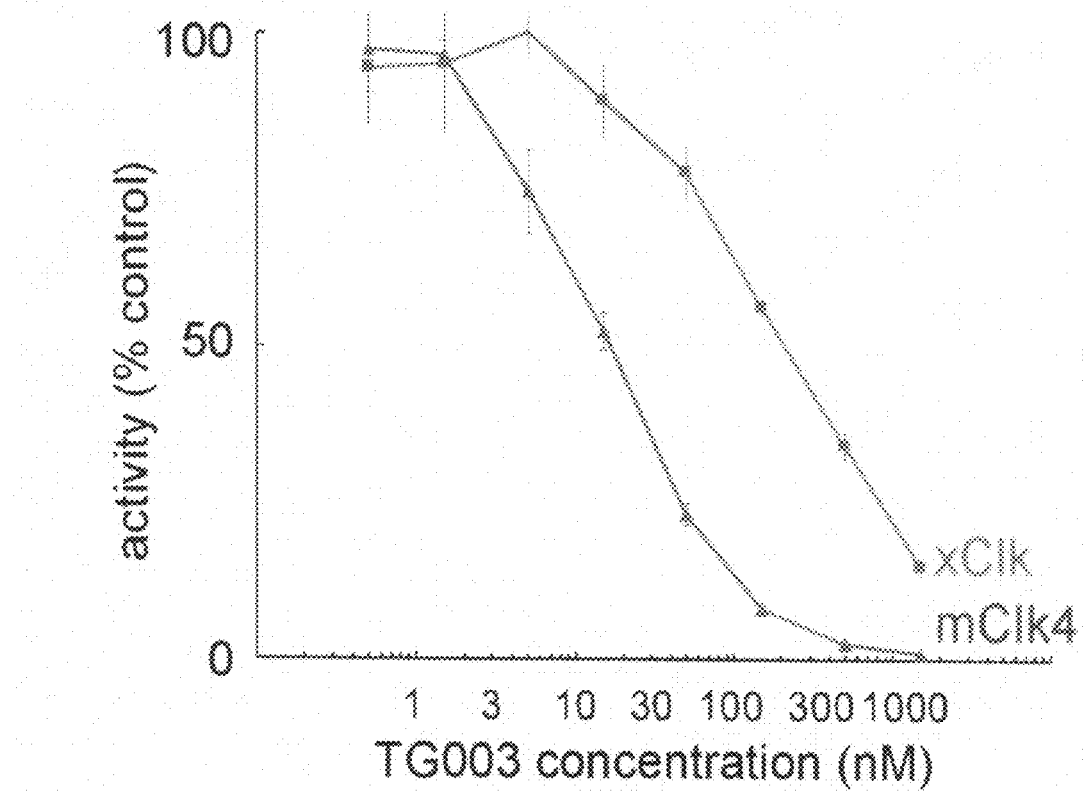
FIG. 6 shows that TG003 rescues the xClk-induced abnormal development of *Xenopus* embryo. A, RT-PCR analysis of *Xenopus* Clk (xClk) mRNA. RNA from two embryos at stage 2, 12, 18, and 40 was analyzed. B, xClk kinase activity is also inhibited by TG003 in vitro. Synthetic peptide for RS domain of SF2/ASF was incubated with recombinant xClk or mouse Clk4 in a reaction mixture with 0-1 μM TG003. The data are means of three independent assays shown with the standard deviation. C, the effect of microinjected xClk mRNA on the body formation of *Xenopus* embryo. Embryos were incubated with Me$_2$SO (DMSO) (panels a and b, and e and f) or 10 μM TG003 (panels c and d, and g and h) until 4-cell stage (stage 3). Synthetic mRNAs containing xClk was injected into the two dorsal blastomeres and further cultured for 2 or 5 days at 22° C. in the dark. D, quantitative summary of developmental defects caused by xClk microinjection. The abnormal embryos at stage 35/36 (day 2) were further classified into two categories: mild phenotype showing short anterior-posterior axis with slight bending, and severe phenotype showing drastic bending often without eye formation.
Figure 6C:
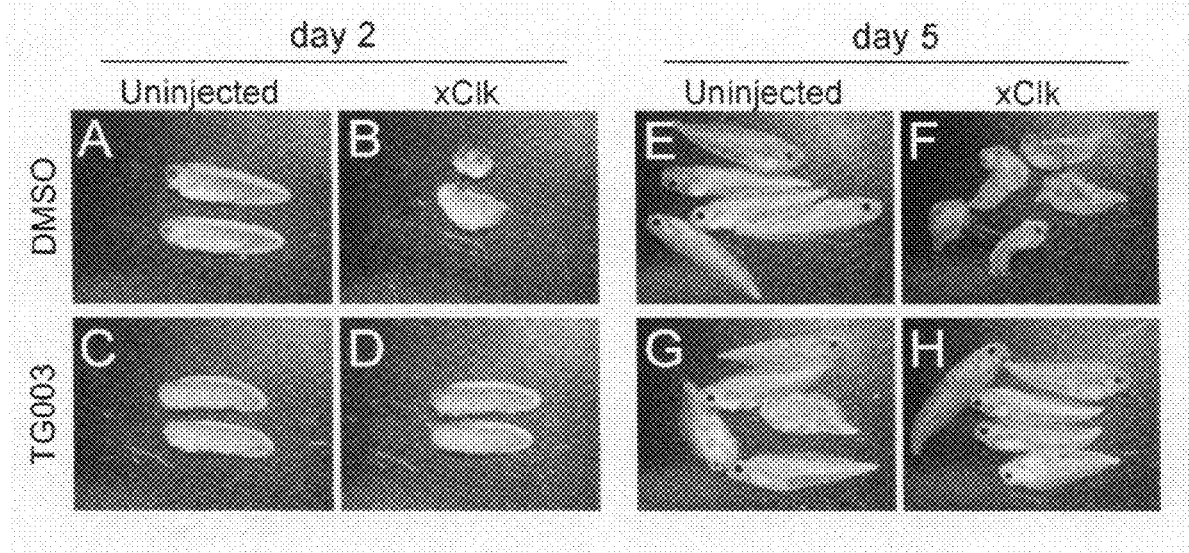
Figure 7A:
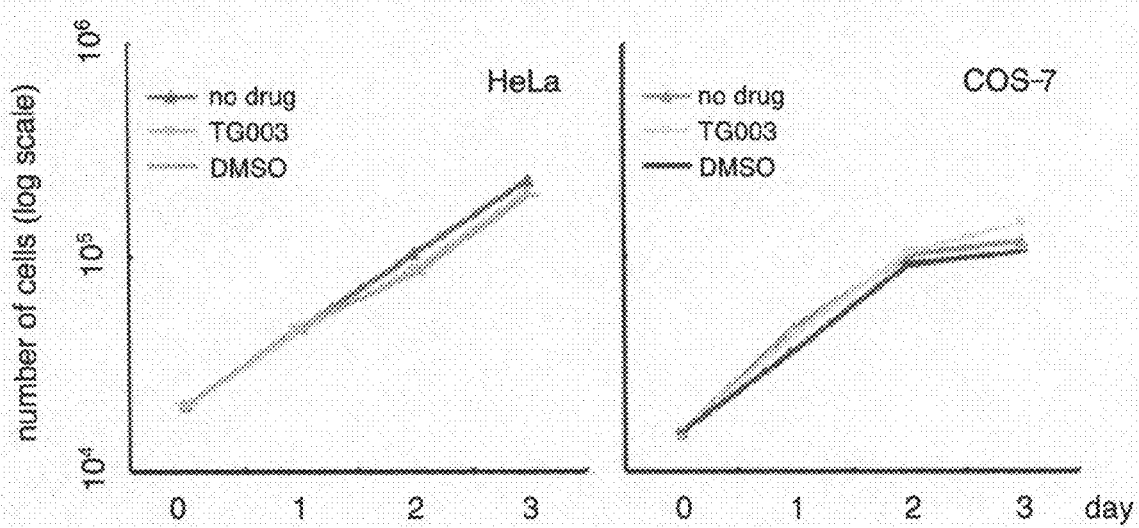
FIG. 7 shows that TG003 has little effects on cell growth. HeLa and COS-7 cells were incubated in the absence or presence of 10 μM TG003, or its solvent (DMSO). The number of cells was counted every 24 hrs for 3 days, and the 3rd days samples were fixed, stained with propidium iodide and the cell cycle profile analyzed by FACS. A. The growth curves of HeLa and COS-7 cells. The average number from duplicated samples is plotted. B. The cell cycle profile. The percentage of cells in G1, S and G2/M is indicated.
Figure 7B:
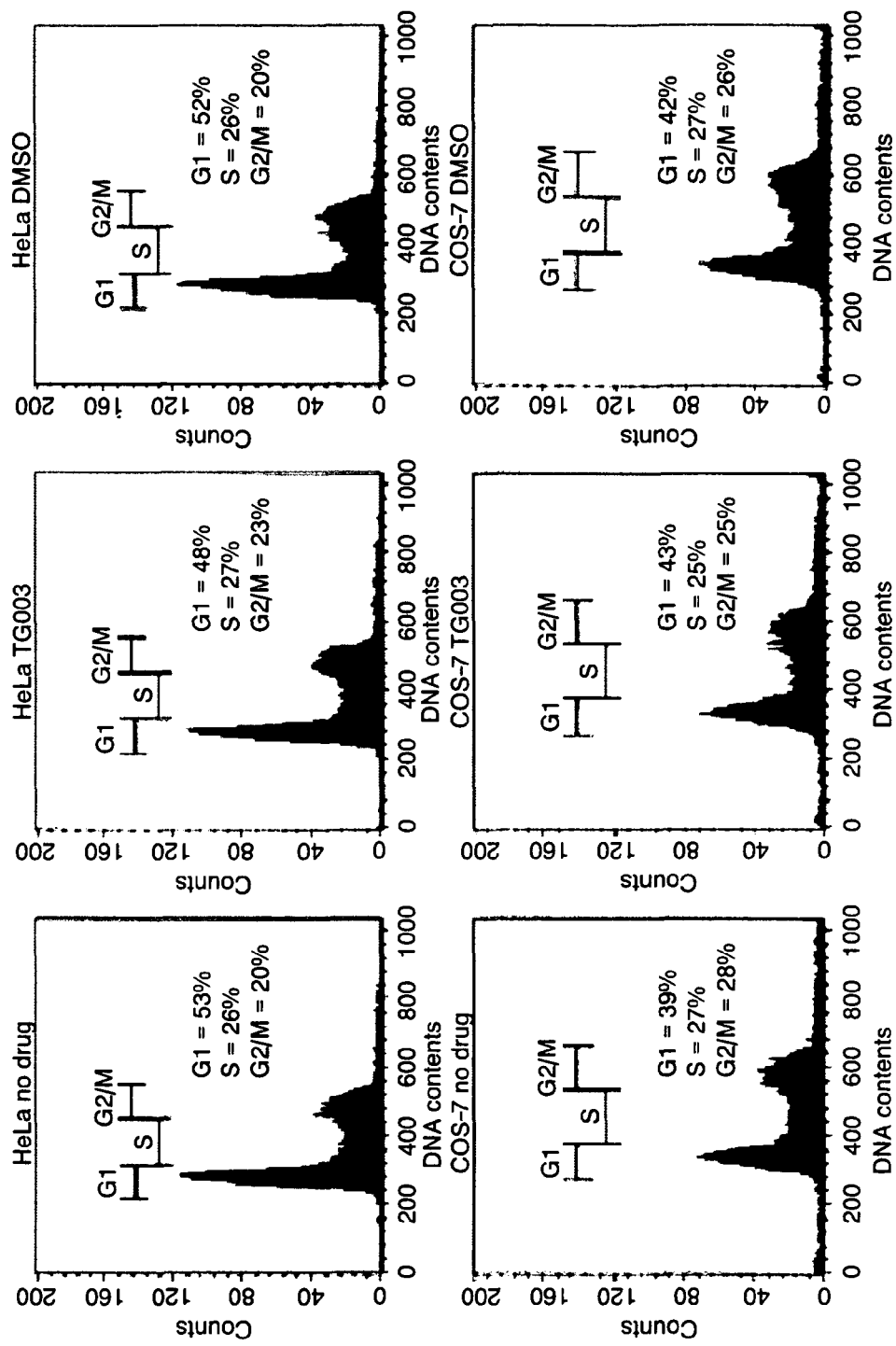

To evaluate the potential use of TG003 in whole animal body, we used X. laevis embryo as a model system. As it was reported that the Drosophila homologue of Clk1/Sty, DOA (darkener of Apricot), is essential during early embryonic development (43, 44), Xenopus Clk homologues could also play important roles during development. In a data base, we found a cDNA sequence of Xenopus Clk (xClk; GenBank™ accession number BC043963), whose amino acid sequence is most homologous to mammalian Clk2 (~70% identity at the amino acid level) in the Clk family (Supplemental Material FIG. 2). By using RT-PCR, the expression of xClk mRNA during early development was analyzed, and it appears through all stages of Xenopus embryos (FIG. 6A). We prepared recombinant xClk protein and found that the kinase activity was sensitive to TG003 at similar dose ranges as mouse Clk2 (FIG. 6B and FIG. 1B). Dorsal injection of xClk mRNA induced morphological abnormalities in the dorsal mesoderm and ectoderm (FIG. 6C, panels b and f), suggesting that an increase in xClk kinase activity disturbs normal embryogenesis. Indeed, the abnormal development phenotype of the Xenopus embryos was rescued when they were incubated with 10 μM TG003 (FIG. 6C, panels d and h, and FIG. 6D).

Discussion

Although a number of studies reported that Clk kinases can modulate the localization and function of SR proteins in the nucleus (17, 23, 24), the biological functions of mammalian Clk remain unknown. It is possible that Clk family kinases are key regulators of SR protein function, which in turn regulate alternative splicing, by phosphorylating SR proteins. Because the phosphorylation also affects the subcellular localization (15) and the stability of a particular SR protein (45), Clk kinase activity can regulate the balance of alternatively spliced forms in a developmental stage- and tissue-specific manner. Clk homologues have been isolated from distantly related species, including Saccharomyces cerevisiae (46), Arabidopsis thaliana (47), and Drosophila melanogaster (43). These kinases share the conserved amino acid motif "EHLAMMERILG" in the kinase subdomain X, which has led these kinases to be dubbed "LAMMER" kinases (43). In Drosophila, Doa protein is required for segmentation and development of the nervous system, and Doa mutations are almost invariably recessive lethal (44). Du et al. (48) showed that mutations in the Doa locus affect sexual differentiation by specifically disrupting sex-specific splicing of doublesex pre-mRNA through a genetic interaction with the SR-like proteins TRA and TRA2. Thus, it is likely that the kinase activity of DOA is regulated depending on the developmental stage. Here, we observed stable expression of xClk in Xenopus embryo, but overexpression of xClk induced embryonic defects. This result suggests that the kinase activity of Clk is tightly regulated during vertebrate embryonic development. Although the regulatory pathways of Clks remain unknown, a regulatory protein that specifically binds to unphosphorylated Clk4 protein was cloned by two-hybrid screening (49). TG003, a specific inhibitor of Clk1/Sty and Clk4, will be a valuable tool to dissect the regulatory mechanisms involving SR protein phosphorylation in vivo and may be applicable for the therapeutic manipulation of abnormal splicing.

To date, a number of diseases caused by mis-splicing have been reported; in some cases, mutation(s) found around splice sites appear to be responsible for changing the splicing pattern of a transcript by unusual exon inclusion or exclusion and/or alteration of 5' or 3' sites (reviewed in Refs. 3-5). A typical example is β-thalassemia, an autosomal recessive disease, which is often associated with mutations in intron 2 of the α-globin gene. The generation of aberrant 5' splice sites activates a common 3' cryptic site upstream of the mutations and induces inclusion of a fragment of the intron-containing stop codon. As a result, the amount of functional α-globin protein is reduced. For therapeutic modulation of alternative splicing, several trials with antisense oligonucleotide (reviewed in Ref. 50), peptide nucleic acid oligonucleotide (51), and RNAi (52, 53) have been reported. These approaches could be useful for manipulating a specific splice site selection of a known target sequence like β-globin (50). However, the aberrant splicing, found in the patients of breast cancer, Wilm's tumor, and amyotrophic lateral sclerosis (ALS), are not always accompanied with mutations around splice sites. In sporadic ALS patients, EAAT2 (excitatory amino acid transporters 2) RNA processing is often aberrant in motor cortex and in spinal cord, the regions specifically affected by the disease. As exon 9 is aberrantly skipped in some ALS patients without any mutation in the gene (54), the disorders could be attributed to abnormalities in regulatory factors of splicing. Actually the balance of alternative splicing products can be affected by changes in the ratio of heterogeneous nuclear ribonucleoprotein and SR proteins (28, 31) and in the phosphorylation state and localization of SR proteins (17, 23). Because the expression of Clk increases the level of SR phosphorylation and leads to exon skipping, suppression of the kinase activity by TG003 may rescue the splicing aberration produced by exon skipping as observed in EAAT2 mRNA. In addition to ALS, TG003 may be applicable for spinal muscular atrophy by increasing an exon inclusion in SMN2 (survival of motor neuron 2) gene to produce functional SMN2 if Clk is involved in SAN2 exon skipping. Some other small molecules (e.g aclarubicin (55) and sodium butyrate (56)) have potency to increase an exon inclusion of SMN2 gene. However, the mechanisms of these effects remain to be unknown. Moreover, because aclarubicin and sodium butylate were found as an anti-cancer reagent and a histone deacetylase inhibitor affecting transcription, respectively, these compounds have obvious pleiotropic effects other than splicing.

As for the inhibitors of Clk family, 5,6-dichloro-1-β-D-ribofuranosylbenzimidazole (DRB) was shown to influence endogenous Clk2 autophosphorylation levels and its subnuclear localization (57). Although DRB has been reported to inhibit the broad range of protein kinases, including casein kinase II (58) and P-TEFb (59), combination of DRB and the newly developed TG003, a specific inhibitor of Clk family kinases, may give us clues to clarify the Clks-mediated signal pathways and their biological functions.

INDUSTRIAL APPLICATION

The pharmaceutical composition of treating or preventing diseases associated with abnormal splicing caused by the excessive kinase induction selected from the group consisting of FTDP-17, NF2, FRASIER, Wilms tumor, breast cancer, ovarian cancer, renal cancer, lung cancer, urothellal cancer, gastric cancer, papillary thyroid cancer, HNSCC, invasive breast cancer, glant cell tumors of bone, prostate cancer, melanoma, lymphoma, oral cancer, pharyngeal cancer and so on.

REFERENCES

In this specification, the references are shown by the number indicated below.

1. Black, D. L. (2000) *Cell* 103, 367.370
2. Modrek, B., and Lee, C. J. (2003) *Nat. Genet.* 34, 177.180
3. Stoss, O., Stoilov, P., Daoud, R., Hartmann, A. M., Olbrich, M., and Stamm, S. (2000) *Gene Ther. Mol. Biol.* 5, 9.30
4. Philips, A. V., and Cooper, T. A. (2000) *Cell. Mol. Life Sci.* 57, 235.249
5. Faustino, N. A., and Cooper, T. A. (2003) *Genes Dev.* 17, 419.437
6. Krawczak, M., Reiss, J., and Cooper, D. N. (1992) *Hum. Genet.* 90, 41.54
7. Stamm, S. (2002) *Hum. Mol. Genet.* 11, 2409.2416
8. Krainer, A. R., Mayeda, A., Kozak, D., and Binns, G. (1991) *Cell* 66, 383.394
9. Blencowe, B. J. (2000) *Trends Biochem. Sci.* 25, 106.110
10. Zahler, A. M., Lane, W. S., Stolk, J. A., and Roth, M. B. (1992) *Genes Dev.* 6, 837.847
11. Caceres, J. F., and Krainer, A. R. (1993) *EMBO J.* 12, 4715.4726
12. Kohtz, J. D., Jamison, S. F., Will, C. L., Zuo, P., Luhrmann, R., Garcia-Blanco, M. A., and Manley, J. L. (1994) *Nature* 368, 119.124
13. Gui, J. F., Lane, W. S., and Fu, X. D. (1994) *Nature* 369, 678.682
14. Xiao, S. H., and Manley, J. L. (1997) *Genes Dev.* 11, 334.344
15. Caceres, J. F., Screaton, G. R., and Krainer, A. R. (1998) *Genes Dev.* 12, 55.66
16. Misteli, T., Caceres, J. F., Clement, J. Q., Krainer, A. R., Wilkinson, M. F., and Spector, D. L. (1998) *J. Cell Biol.* 143, 297.307
17. Duncan, P. I., Stojdl, D. F., Marius, R. M., and Bell, J. C. (1997) *Mol. Cell. Biol.* 17, 5996.6001
18. Cao, W., Jamison, S. F., and Garcia-Blanco, M. A. (1997) *RNA* (New York) 3, 1456.1467
19. Gui, J. F., Tronchere, H., Chandler, S. D., and Fu, X. D. (1994) *Proc. Natl. Acad. Sci. U.S.A.* 91, 10824.10828
20. Kuroyanagi, N., Onogi, H., Wakabayashi, T., and Hagiwara, M. (1998) *Biochem. Biophys. Res. Commun.* 242, 357.364
21. Kojima, T., Zama, T., Wada, K., Onogi, H., and Hagiwara, M. (2001) *J. Biol. Chem.* 276, 32247.32256
22. Rossi, F., Labourier, E., Forne, T., Divita, G., Derancourt, J., Riou, J. F., Antoine, E., Cathala, G., Brunel, C., and Tazi, J. (1996) *Nature* 381, 80.82
23. Colwill, K., Pawson, T., Andrews, B., Prasad, J., Manley, J. L., Bell, J. C., and Duncan, P. I. (1996) *EMBO J.* 15, 265.275
24. Nayler, O., Stamm, S., and Ullrich, A. (1997) *Biochem. J.* 326, 693.700
25. Ben-David, Y., Letwin, K., Tannock, L., Bernstein, A., and Pawson, T. (1991) *EMBO J.* 10, 317.325
26. Howell, B. W., Afar, D. E., Lew, J., Douville, E. M., Icely, P. L., Gray, D. A., and Bell, J. C. (1991) *Mol. Cell. Biol.* 11, 568.572
27. Gupta, A. K., Ben-Mahmud, A., Kamphuis, L. J., Mueller, J. L., Rigby, S. S., Gibson, M. S., Richardson, M. F., Humeniuk, L., and Walker, S. (1995) *Can. J. Chem.* 73, 1278.1286
28. Mayeda, A., and Krainer, A. R. (1992) *Cell* 68, 365.375
29. Mayeda, A., and Krainer, A. R. (1999) *Methods Mol. Biol.* 118, 309.314
30. Hagiwara, M., Inagaki, M., and Hidaka, H. (1987) *Mol. Pharmacol.* 31, 523.528
31. Caceres, J. F., Stamm, S., Helfman, D. M., and Krainer, A. R. (1994) *Science* 265, 1706.1709
32. Pilch, B., Allemand, E., Facompre, M., Bailly, C., Riou, J. F., Soret, J., and Tazi, J. (2001) *Cancer Res.* 61, 6876.6884
33. Rupp, R. A., Snider, L., and Weintraub, H. (1994) *Genes Dev.* 8, 1311.1323
34. Masuyama, N., Hanafusa, H., Kusakabe, M., Shibuya, H., and Nishida, E. (1999) *J. Biol. Chem.* 274, 12163.12170
35. Nieuwkoop, P. D., and Faber, J. (1956) *Normal Table of Xenopus laevis* (Daudin), Elsevier/North-Holland Biomedical Press, Amsterdam
36. Mermoud, J. E., Cohen, P. T., and Lamond, A. I. (1994) *EMBO J.* 13, 5679.5688
37. Hanamura, A., Caceres, J. F., Mayeda, A., Franza, B. R., Jr., and Krainer, A. R. (1998) *RNA* (New York) 4, 430.444
38. Lamond, A. I., and Spector, D. L. (2003) *Nat. Rev. Mol. Cell Biol.* 4, 605.612
39. Neugebauer, K. M., and Roth, M. B. (1997) *Genes Dev.* 11, 1148.1159
40. Roth, M. B., Zahler, A. M., and Stolk, J. A. (1991) *J. Cell Biol.* 115, 5877.5896
41. Berk, A. J., and Sharp, P. A. (1978) *Cell* 14, 695.711
42. Soret, J., Gabut, M., Dupon, C., Kohlhagen, G., Stevenin, J., Pommier, Y., and Tazi, J. (2003) *Cancer Res.* 63, 8203.8211
43. Yun, B., Farkas, R., Lee, K., and Rabinow, L. (1994) *Genes Dev.* 8, 1160.1173
44. Rabinow, L., Chiang, S. L., and Birchler, J. A. (1993) *Genetics* 134, 1175.1185
45. Lai, M. C., Lin, R. I., and Tarn, W. Y. (2003) *Biochem. J.* 371, 937.945
46. Lee, K., Du, C., Horn, M., and Rabinow, L. (1996) *J. Biol. Chem.* 271, 27299.27303
47. Bender, J., and Fink, G. R. (1994) *Proc. Natl. Acad. Sci. U.S.A.* 91, 12105.12109
48. Du, C., McGuffin, M. E., Dauwalder, B., Rabinow, L., and Mattox, W. (1998) *Mol. Cell* 2, 741.750
49. Katsu, R., Onogi, H., Wada, K., Kawaguchi, Y., and Hagiwara, M. (2002) *J. Biol. Chem.* 277, 44220.44228
50. Sazani, P., and Kole, R. (2003) *J. Clin. Investig.* 112, 481.486
51. Cartegni, L., and Krainer, A. R. (2003) *Nat. Struct. Biol.* 10, 120.125
52. Epstein, P. M. (1998) *Methods* 14, 21.33
53. Celotto, A. M., and Graveley, B. R. (2002) *RNA* (New York) 8, 718.724
54. Lin, C. L., Bristol, L. A., Jin, L., Dykes-Hoberg, M., Crawford, T., Clawson, L., and Rothstein, J. D. (1998) *Neuron* 20, 589.602
55. Andreassi, C., Jarecki, J., Zhou, J., Coovert, D. D., Monani, U. R., Chen, X., Whitney, M., Pollok, B., Zhang, M., Androphy, E., and Burghes, A. H. (2001) *Hum. Mol. Genet.* 10, 2841.2849
56. Chang, J. G., Hsieh-Li, H. M., Jong, Y. J., Wang, N. M., Tsai, C. H., and Li, H. (2001) *Proc. Natl. Acad. Sci. U.S.A.* 98, 9808.9813
57. Nayler, O., Schnorrer, F., Stamm, S., and Ullrich, A. (1998) *J. Biol. Chem.* 273, 34341.34348
58. Zandomeni, R., Zandomeni, M. C., Shugar, D., and Weinmann, R. (1986) *J. Biol. Chem.* 261, 3414.3419.
59. Marshall, N. F., and Price, D. H. (1995) *J. Biol. Chem.* 270, 12335.12338

The invention claimed is:

1. A pharmaceutical composition, which comprises a benzothiazol compound represented by formula I

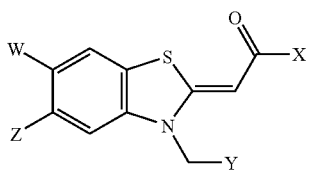

wherein X and Y are independently linear or branched $C_1$-$C_{10}$ hydrocarbon chain, and z is methoxy, ethoxy, acetoxy or fluorine, and W is H.

2. The pharmaceutical composition according to claim 1, wherein the benzothiazol compound is TG003.

3. A method of inhibiting Clk1, Clk2 and/or Clk4 activity, which comprises administering to a patient in need thereof a benzothiazol compound represented by formula I,

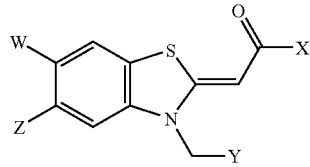

wherein X and Y are independently linear or branched $C_1$-$C_{10}$ hydrocarbon chain, and Z is methoxy, ethoxy, acetoxy or halogen and W is H.

4. The method according to claim 3, wherein the benzothiazol compound is TG003.

5. A method of treating diseases associated with excessive Clk1, Clk2, and/or Clk4 activity, which comprises administering to a patient in need thereof an effective amount of the pharmaceutical composition according to claim 1.

6. A method of inhibiting Clk1, Clk2, and/or Clk4 activity, which comprises contacting a Clk1, Clk2, and/or Clk4 with the pharmaceutical composition according to claim 1.

* * * * *

SEQUENCE LISTING

<160> NUMBER OF SEQ ID NOS: 13

<210> SEQ ID NO 1
<211> LENGTH: 29
<212> TYPE: PRT
<213> ORGANISM: Artificial Sequence
<220> FEATURE:
<223> OTHER INFORMATION: synthetic peptide of SF2/ASF RS domain

<400> SEQUENCE: 1

Arg Ser Pro Ser Tyr Gly Arg Ser Arg Ser Arg Ser Arg Ser
1               5                   10                  15

Arg Ser Arg Ser Arg Ser Asn Ser Arg Ser Arg Ser Tyr
            20                  25

<210> SEQ ID NO 2
<211> LENGTH: 30
<212> TYPE: DNA
<213> ORGANISM: Artificial Sequence
<220> FEATURE:
<223> OTHER INFORMATION: 5' primer designed according to the IMAGE clone
      of xClk

<400> SEQUENCE: 2
atgcctcact ccagacgtta cggttcgtca                                        30

<210> SEQ ID NO 3
<211> LENGTH: 30
<212> TYPE: DNA
<213> ORGANISM: Artificial Sequence
<220> FEATURE:
<223> OTHER INFORMATION: 3' primer designed according to the IMAGE clone
      of xClk

<400> SEQUENCE: 3
tcatcggctt atgtcccggc cagtgtccca                                        30

<210> SEQ ID NO 4
<211> LENGTH: 484
<212> TYPE: PRT
<213> ORGANISM: Homo sapiens

<400> SEQUENCE: 4

Met Arg His Ser Lys Arg Thr Tyr Cys Pro Asp Trp Asp Lys Asp
1               5                   10                  15

Trp Asp Tyr Gly Lys Trp Arg Ser Ser Ser His Lys Arg Arg Lys
            20                  25                  30

Arg Ser His Ser Ser Ala Gln Glu Asn Lys Arg Cys Lys Tyr Asn His
                35                  40                  45

Ser Lys Met Cys Asp Ser His Tyr Leu Glu Ser Arg Ser Ile Asn Glu
    50                  55                  60

Lys Asp Tyr His Ser Arg Arg Tyr Ile Asp Glu Tyr Arg Asn Asp Tyr
65                  70                  75                  80

Thr Gln Gly Cys Glu Pro Gly His Arg Gln Arg Asp His Glu Ser Arg
                85                  90                  95

Tyr Gln Asn His Ser Ser Lys Ser Ser Gly Arg Ser Gly Arg Ser Ser
                100                 105                 110

Tyr Lys Ser Lys His Arg Ile His His Ser Thr Ser His Arg Arg Ser
        115                 120                 125

His Gly Lys Ser His Arg Arg Lys Arg Thr Arg Ser Val Glu Asp Asp

```
                130             135             140
Glu Glu Gly His Leu Ile Cys Gln Ser Gly Asp Val Leu Ser Ala Arg
145                 150                 155                 160

Tyr Glu Ile Val Asp Thr Leu Gly Gly Ala Phe Gly Lys Val Val
                165                 170                 175

Glu Cys Ile Asp His Lys Ala Gly Gly Arg His Val Ala Val Lys Ile
                180                 185                 190

Val Lys Asn Val Asp Arg Tyr Cys Glu Ala Ala Arg Ser Glu Ile Gln
                195                 200                 205

Val Leu Glu His Leu Asn Thr Thr Asp Pro Asn Ser Thr Phe Arg Cys
210                 215                 220

Val Gln Met Leu Glu Trp Phe Glu His His Gly His Ile Cys Ile Val
225                 230                 235                 240

Phe Glu Leu Leu Gly Leu Ser Thr Tyr Asp Phe Ile Lys Glu Asn Gly
                245                 250                 255

Phe Leu Pro Phe Arg Leu Asp His Ile Arg Lys Met Ala Tyr Gln Ile
                260                 265                 270

Cys Lys Ser Val Asn Phe Leu His Ser Asn Lys Leu Thr His Thr Asp
                275                 280                 285

Leu Lys Pro Glu Asn Ile Leu Phe Val Gln Ser Asp Tyr Thr Glu Ala
                290                 295                 300

Tyr Asn Pro Lys Ile Lys Arg Asp Glu Arg Thr Leu Ile Asn Pro Asp
305                 310                 315                 320

Ile Lys Val Val Asp Phe Gly Ser Ala Thr Tyr Asp Asp Glu His His
                325                 330                 335

Ser Thr Leu Val Ser Thr Arg His Tyr Arg Ala Pro Glu Val Ile Leu
                340                 345                 350

Ala Leu Gly Trp Ser Gln Pro Cys Asp Val Trp Ser Ile Gly Cys Ile
                355                 360                 365

Leu Ile Glu Tyr Tyr Leu Gly Phe Thr Val Phe Pro Thr His Asp Ser
                370                 375                 380

Lys Glu His Leu Ala Met Met Glu Arg Ile Leu Gly Pro Leu Pro Lys
385                 390                 395                 400

His Met Ile Gln Lys Thr Arg Lys Arg Lys Tyr Phe His His Asp Arg
                405                 410                 415

Leu Asp Trp Asp Glu His Ser Ser Ala Gly Arg Tyr Val Ser Arg Arg
                420                 425                 430

Cys Lys Pro Leu Lys Glu Phe Met Leu Ser Gln Asp Val Glu His Glu
                435                 440                 445

Arg Leu Phe Asp Leu Ile Gln Lys Met Leu Glu Tyr Asp Pro Ala Lys
                450                 455                 460

Arg Ile Thr Leu Arg Glu Ala Leu Lys His Pro Phe Phe Asp Leu Leu
465                 470                 475                 480

Lys Lys Ser Ile

<210> SEQ ID NO 5
<211> LENGTH: 499
<212> TYPE: PRT
<213> ORGANISM: Homo sapiens

<400> SEQUENCE: 5

Met Pro His Pro Arg Arg Tyr His Ser Ser Glu Arg Gly Ser Arg Gly
1               5                   10                  15

Ser Tyr Arg Glu His Tyr Arg Ser Arg Lys His Lys Arg Arg Arg Ser
```

-continued

```
                 20                  25                  30
Arg Ser Trp Ser Ser Ser Asp Arg Thr Arg Arg Arg Glu
             35                  40                  45
Asp Ser Tyr His Val Arg Ser Arg Ser Tyr Asp Asp Arg Ser Ser
 50                  55                  60
Asp Arg Arg Val Tyr Asp Arg Arg Tyr Cys Gly Ser Tyr Arg Asn
 65                  70                  75                  80
Asp Tyr Ser Arg Asp Arg Gly Asp Ala Tyr Tyr Asp Thr Asp Tyr Arg
                 85                  90                  95
His Ser Tyr Glu Tyr Gln Arg Glu Asn Ser Ser Tyr Ser Gln Arg
                100                 105                 110
Ser Ser Arg Arg Lys His Arg Arg Arg Arg Ser Arg Thr Phe
             115                 120                 125
Ser Arg Ser Ser Ser Gln His Ser Ser Arg Arg Ala Lys Ser Val Glu
 130                 135                 140
Asp Asp Ala Glu Gly His Leu Ile Tyr His Val Gly Asp Trp Leu Gln
 145                 150                 155                 160
Glu Arg Tyr Glu Ile Val Ser Thr Leu Gly Glu Gly Thr Phe Gly Arg
                 165                 170                 175
Val Val Gln Cys Val Asp His Arg Arg Gly Gly Ala Arg Val Ala Leu
             180                 185                 190
Lys Ile Ile Lys Asn Val Glu Lys Tyr Lys Glu Ala Ala Arg Leu Glu
         195                 200                 205
Ile Asn Val Leu Glu Lys Ile Asn Glu Lys Asp Pro Asp Asn Lys Asn
 210                 215                 220
Leu Cys Val Gln Met Phe Asp Trp Phe Asp Tyr His Gly His Met Cys
 225                 230                 235                 240
Ile Ser Phe Glu Leu Leu Gly Leu Ser Thr Phe Asp Phe Leu Lys Asp
             245                 250                 255
Asn Asn Tyr Leu Pro Tyr Pro Ile His Gln Val Arg His Met Ala Phe
             260                 265                 270
Gln Leu Cys Gln Ala Val Lys Phe Leu His Asp Asn Lys Leu Thr His
             275                 280                 285
Thr Asp Leu Lys Pro Glu Asn Ile Leu Phe Val Asn Ser Asp Tyr Glu
 290                 295                 300
Leu Thr Tyr Asn Leu Glu Lys Lys Arg Asp Glu Arg Ser Val Lys Ser
 305                 310                 315                 320
Thr Ala Val Arg Val Val Asp Phe Gly Ser Ala Thr Phe Asp His Glu
                 325                 330                 335
His His Ser Thr Ile Val Ser Thr Arg His Tyr Arg Ala Pro Glu Val
             340                 345                 350
Ile Leu Glu Leu Gly Trp Ser Gln Pro Cys Asp Val Trp Ser Ile Gly
         355                 360                 365
Cys Ile Ile Phe Glu Tyr Tyr Val Gly Phe Thr Leu Phe Gln Thr His
             370                 375                 380
Asp Asn Arg Glu His Leu Ala Met Met Glu Arg Ile Leu Gly Pro Ile
 385                 390                 395                 400
Pro Ser Arg Met Ile Arg Lys Thr Arg Lys Gln Lys Tyr Phe Tyr Arg
                 405                 410                 415
Gly Arg Leu Asp Trp Asp Glu Asn Thr Ser Ala Gly Arg Tyr Val Arg
             420                 425                 430
Glu Asn Cys Lys Pro Leu Arg Arg Tyr Leu Thr Ser Glu Ala Glu Glu
             435                 440                 445
```

His His Gln Leu Phe Asp Leu Ile Glu Ser Met Leu Glu Tyr Glu Pro
              450                 455                 460

Ala Lys Arg Leu Thr Leu Gly Glu Ala Leu Gln His Pro Phe Phe Ala
465                 470                 475                 480

Arg Leu Arg Ala Glu Pro Pro Asn Lys Leu Trp Asp Ser Ser Arg Asp
                    485                 490                 495

Ile Ser Arg

<210> SEQ ID NO 6
<211> LENGTH: 490
<212> TYPE: PRT
<213> ORGANISM: Homo sapiens

<400> SEQUENCE: 6

Met His His Cys Lys Arg Tyr Arg Ser Pro Glu Pro Asp Pro Tyr Leu
1               5                   10                  15

Ser Tyr Arg Trp Lys Arg Arg Ser Tyr Ser Arg Glu His Glu Gly
            20                  25                  30

Arg Leu Arg Tyr Pro Ser Arg Arg Glu Pro Pro Arg Arg Ser Arg
                35                  40                  45

Ser Arg Ser His Asp Arg Leu Pro Tyr Gln Arg Arg Tyr Arg Glu Arg
    50                  55                  60

Arg Asp Ser Asp Thr Tyr Arg Cys Glu Glu Arg Ser Pro Ser Phe Gly
65                  70                  75                  80

Glu Asp Tyr Tyr Gly Pro Ser Ser Arg His Arg Arg Ser Arg
                85                  90                  95

Glu Arg Gly Pro Tyr Arg Thr Arg Lys His Ala His His Cys His Lys
                100                 105                 110

Arg Thr Arg Ser Cys Ser Ser Ala Ser Ser Arg Ser Gln Gln Ser
            115                 120                 125

Ser Lys Arg Thr Gly Arg Ser Val Glu Asp Asp Lys Glu Gly His Leu
            130                 135                 140

Val Cys Arg Ile Gly Asp Trp Leu Gln Glu Arg Tyr Glu Ile Val Gly
145                 150                 155                 160

Asn Leu Gly Glu Gly Thr Phe Gly Lys Val Val Glu Cys Leu Asp His
                165                 170                 175

Ala Arg Gly Lys Ser Gln Val Ala Leu Lys Ile Ile Arg Asn Val Gly
                180                 185                 190

Lys Tyr Arg Glu Ala Ala Arg Leu Glu Ile Asn Val Leu Lys Lys Ile
            195                 200                 205

Lys Glu Lys Asp Lys Glu Asn Lys Phe Leu Cys Val Leu Met Ser Asp
            210                 215                 220

Trp Phe Asn Phe His Gly His Met Cys Ile Ala Phe Glu Leu Leu Gly
225                 230                 235                 240

Lys Asn Thr Phe Glu Phe Leu Lys Glu Asn Asn Phe Gln Pro Tyr Pro
                245                 250                 255

Leu Pro His Val Arg His Met Ala Tyr Gln Leu Cys His Ala Leu Arg
                260                 265                 270

Phe Leu His Glu Asn Gln Leu Thr His Thr Asp Leu Lys Pro Glu Asn
            275                 280                 285

Ile Leu Phe Val Asn Ser Glu Phe Glu Thr Leu Tyr Asn Glu His Lys
            290                 295                 300

Ser Cys Glu Glu Lys Ser Val Lys Asn Thr Ser Ile Arg Val Ala Asp
305                 310                 315                 320

-continued

Phe Gly Ser Ala Thr Phe Asp His Glu His Thr Thr Ile Val Ala
                325                 330                 335

Thr Arg His Tyr Arg Pro Pro Glu Val Ile Leu Glu Leu Gly Trp Ala
                340                 345                 350

Gln Pro Cys Asp Val Trp Ser Ile Gly Cys Ile Leu Phe Glu Tyr Tyr
                355                 360                 365

Arg Gly Phe Thr Leu Phe Gln Thr His Glu Asn Arg Glu His Leu Val
            370                 375                 380

Met Met Glu Lys Ile Leu Gly Pro Ile Pro Ser His Met Ile His Arg
385                 390                 395                 400

Thr Arg Lys Gln Lys Tyr Phe Tyr Lys Gly Leu Val Trp Asp Glu
                405                 410                 415

Asn Ser Ser Asp Gly Arg Tyr Val Lys Glu Asn Cys Lys Pro Leu Lys
                420                 425                 430

Ser Tyr Met Leu Gln Asp Ser Leu Glu His Val Gln Leu Phe Asp Leu
            435                 440                 445

Met Arg Arg Met Leu Glu Phe Asp Pro Ala Gln Arg Ile Thr Leu Ala
        450                 455                 460

Glu Ala Leu Leu His Pro Phe Phe Ala Gly Leu Thr Pro Glu Glu Arg
465                 470                 475                 480

Ser Phe His Thr Ser Arg Asn Pro Ser Arg
                485                 490

<210> SEQ ID NO 7
<211> LENGTH: 453
<212> TYPE: PRT
<213> ORGANISM: Homo sapiens

<400> SEQUENCE: 7

Met Arg His Ser Lys Arg Thr Tyr Cys Pro Asp Trp Asp Asp Lys Asp
1               5                   10                  15

Trp Asp Tyr Gly Lys Trp Arg Ser Ser Ser Ser His Lys Arg Arg Lys
                20                  25                  30

Arg Ser His Ser Ser Ala Gln Glu Asn Lys Arg Cys Lys Tyr Asn His
            35                  40                  45

Ser Lys Met Cys Asp Ser His Tyr Leu Glu Ser Arg Ser Ile Asn Glu
        50                  55                  60

Lys Asp Tyr His Ser Arg Arg Tyr Ile Asp Glu Tyr Arg Asn Asp Tyr
65                  70                  75                  80

Thr Gln Gly Cys Glu Pro Gly His Arg Gln Arg Asp His Glu Ser Arg
                85                  90                  95

Tyr Gln Asn His Ser Ser Lys Ser Ser Gly Arg Ser Gly Arg Ser Ser
            100                 105                 110

Tyr Lys Ser Lys His Arg Ile His His Ser Thr Ser His Arg Arg Ser
        115                 120                 125

His Gly Asp Glu Ile Val Asp Thr Leu Gly Glu Gly Ala Phe Gly Lys
    130                 135                 140

Val Val Glu Cys Ile Asp His Lys Ala Gly Gly Arg His Val Ala Val
145                 150                 155                 160

Lys Ile Val Lys Asn Val Asp Arg Tyr Cys Glu Ala Ala Arg Ser Glu
                165                 170                 175

Ile Gln Val Leu Glu His Leu Asn Thr Thr Asp Pro Asn Ser Thr Phe
            180                 185                 190

Arg Cys Val Gln Met Leu Glu Trp Phe Glu His His Gly His Ile Cys

-continued

```
                195                 200                 205
Ile Val Phe Glu Leu Leu Gly Leu Ser Thr Tyr Asp Phe Ile Lys Glu
    210                 215                 220

Asn Gly Phe Leu Pro Phe Arg Leu Asp His Ile Arg Lys Met Ala Tyr
225                 230                 235                 240

Gln Ile Cys Lys Ser Val Asn Phe Leu His Ser Asn Lys Leu Thr His
                245                 250                 255

Thr Asp Leu Lys Pro Glu Asn Ile Leu Phe Val Gln Ser Asp Tyr Thr
            260                 265                 270

Glu Ala Tyr Asn Pro Lys Ile Lys Arg Asp Glu Arg Thr Leu Ile Asn
        275                 280                 285

Pro Asp Ile Lys Val Val Asp Phe Gly Ser Ala Thr Tyr Asp Asp Glu
    290                 295                 300

His His Ser Thr Leu Val Ser Thr Arg His Tyr Arg Ala Pro Glu Val
305                 310                 315                 320

Ile Leu Ala Leu Gly Trp Ser Gln Pro Cys Asp Val Trp Ser Ile Gly
                325                 330                 335

Gly Ile Leu Asn Glu Tyr Tyr Leu Gly Phe Thr Val Phe Gln Thr His
            340                 345                 350

Asp Ser Lys Glu His Leu Ala Met Met Glu Arg Ile Leu Gly Pro Ile
        355                 360                 365

Pro Gln His Met Ile Gln Lys Thr Arg Lys Arg Lys Tyr Phe His His
    370                 375                 380

Asn Gln Leu Asp Trp Asp Glu His Ser Ser Ala Gly Arg Tyr Val Arg
385                 390                 395                 400

Arg Arg Cys Lys Pro Leu Lys Glu Phe Met Leu Cys His Asp Glu Glu
                405                 410                 415

His Glu Lys Leu Phe Asp Leu Val Arg Arg Met Leu Glu Tyr Asp Pro
            420                 425                 430

Thr Gln Arg Ile Thr Leu Asp Glu Ala Leu Gln His Pro Phe Phe Asp
        435                 440                 445

Leu Leu Lys Lys Lys
    450

<210> SEQ ID NO 8
<211> LENGTH: 483
<212> TYPE: PRT
<213> ORGANISM: Mus musculus

<400> SEQUENCE: 8

Met Arg His Ser Lys Arg Thr Tyr Cys Pro Asp Trp Asp Glu Arg Asp
1               5                   10                  15

Trp Asp Tyr Gly Thr Trp Arg Ser Ser Ser His Lys Arg Lys Lys
            20                  25                  30

Arg Ser His Ser Ser Ala Arg Glu Gln Lys Arg Cys Arg Tyr Asp His
        35                  40                  45

Ser Lys Thr Thr Asp Ser Tyr Tyr Leu Glu Ser Arg Ser Ile Asn Glu
    50                  55                  60

Lys Ala Tyr His Ser Arg Arg Tyr Val Asp Glu Tyr Arg Asn Asp Tyr
65                  70                  75                  80

Met Gly Tyr Glu Pro Gly His Pro Tyr Gly Pro Gly Ser Arg Tyr
                85                  90                  95

Gln Met His Ser Ser Lys Ser Ser Gly Arg Ser Gly Arg Ser Ser Tyr
            100                 105                 110
```

```
Lys Ser Lys His Arg Ser Arg His Thr Ser Gln His His Ser His
        115                 120                 125

Gly Lys Ser His Arg Arg Lys Arg Ser Arg Ser Val Glu Asp Asp Glu
        130                 135                 140

Glu Gly His Leu Ile Cys Gln Ser Gly Asp Val Leu Ser Ala Arg Tyr
145                 150                 155                 160

Glu Ile Val Asp Thr Leu Gly Glu Gly Ala Phe Gly Lys Val Val Glu
                165                 170                 175

Cys Ile Asp His Lys Val Gly Gly Arg Arg Val Ala Val Lys Ile Val
                180                 185                 190

Lys Asn Val Asp Arg Tyr Cys Glu Ala Ala Gln Ser Glu Ile Gln Val
                195                 200                 205

Leu Glu His Leu Asn Thr Thr Asp Pro His Ser Thr Phe Arg Cys Val
        210                 215                 220

Gln Met Leu Glu Trp Phe Glu His Arg Gly His Ile Cys Ile Val Phe
225                 230                 235                 240

Glu Leu Leu Gly Leu Ser Thr Tyr Asp Phe Ile Lys Glu Asn Ser Phe
                245                 250                 255

Leu Pro Phe Arg Met Asp His Ile Arg Lys Met Ala Tyr Gln Ile Cys
                260                 265                 270

Lys Ser Val Asn Phe Leu His Ser Asn Lys Leu Thr His Thr Asp Leu
        275                 280                 285

Lys Pro Glu Asn Ile Leu Phe Val Lys Ser Asp Tyr Thr Glu Ala Tyr
        290                 295                 300

Asn Pro Lys Met Lys Arg Asp Glu Arg Thr Ile Val Asn Pro Asp Ile
305                 310                 315                 320

Lys Val Val Asp Phe Gly Ser Ala Thr Tyr Asp Asp Glu His His Ser
                325                 330                 335

Thr Leu Val Ser Thr Arg His Tyr Arg Ala Pro Glu Val Ile Leu Ala
                340                 345                 350

Leu Gly Trp Ser Gln Pro Cys Asp Val Trp Ser Ile Gly Cys Ile Leu
        355                 360                 365

Ile Glu Tyr Tyr Leu Gly Phe Thr Val Phe Pro Thr His Asp Ser Arg
        370                 375                 380

Glu His Leu Ala Met Met Glu Arg Ile Leu Gly Pro Leu Pro Lys His
385                 390                 395                 400

Met Ile Gln Lys Thr Arg Lys Arg Arg Tyr Phe His His Asp Arg Leu
                405                 410                 415

Asp Trp Asp Glu His Ser Ser Ala Gly Arg Tyr Val Ser Arg Arg Cys
                420                 425                 430

Lys Pro Leu Lys Glu Phe Met Leu Ser Gln Asp Ala Glu His Glu Phe
        435                 440                 445

Leu Phe Asp Leu Val Gly Lys Ile Leu Glu Tyr Asp Pro Ala Lys Arg
450                 455                 460

Ile Thr Leu Lys Glu Ala Leu Lys His Pro Phe Phe Tyr Pro Leu Lys
465                 470                 475                 480

Lys His Thr
```

<210> SEQ ID NO 9
<211> LENGTH: 499
<212> TYPE: PRT
<213> ORGANISM: Mus musculus

<400> SEQUENCE: 9

```
Met Pro His Pro Arg Tyr His Ser Ser Glu Arg Gly Ser Arg Gly
1               5                   10                  15

Ser Tyr His Glu His Tyr Gln Ser Arg Lys His Lys Arg Arg Ser
                20                  25                  30

Arg Ser Trp Ser Ser Ser Asp Arg Thr Arg Arg Arg Arg Arg Glu
            35                  40                  45

Asp Ser Tyr His Val Arg Ser Arg Ser Tyr Asp Asp His Ser Ser
    50                  55                  60

Asp Arg Arg Leu Tyr Asp Arg Arg Tyr Cys Gly Ser Tyr Arg Arg Asn
65                  70                  75                  80

Asp Tyr Ser Arg Asp Arg Gly Glu Ala Tyr Tyr Asp Thr Asp Phe Arg
                85                  90                  95

Gln Ser Tyr Glu Tyr His Arg Glu Asn Ser Ser Tyr Arg Ser Gln Arg
                100                 105                 110

Ser Ser Arg Arg Lys His Arg Arg Arg Arg Ser Arg Thr Phe
        115                 120                 125

Ser Arg Ser Ser Ser His Ser Ser Arg Arg Ala Lys Ser Val Glu Asp
    130                 135                 140

Asp Ala Glu Gly His Leu Ile Tyr His Val Gly Asp Trp Leu Gln Glu
145                 150                 155                 160

Arg Tyr Glu Ile Val Ser Thr Leu Gly Glu Gly Thr Ser Gly Arg Val
                165                 170                 175

Val Gln Cys Val Asp His Arg Arg Gly Gly Thr Arg Val Ala Leu Lys
                180                 185                 190

Ile Ile Lys Asn Val Glu Lys Tyr Lys Glu Ala Ala Arg Leu Glu Ile
        195                 200                 205

Asn Val Leu Glu Lys Ile Asn Glu Lys Asp Pro Asp Asn Lys Asn Leu
    210                 215                 220

Cys Val Gln Met Phe Asp Trp Phe Asp Tyr His Gly His Met Cys Ile
225                 230                 235                 240

Ser Phe Glu Leu Leu Gly Leu Ser Thr Phe Asp Phe Leu Lys Asp Asn
                245                 250                 255

Asn Tyr Leu Pro Tyr Pro Ile His Gln Val Arg His Met Ala Phe Gln
                260                 265                 270

Leu Cys Gln Ala Val Lys Phe Leu His Asp Asn Lys Leu Thr His Thr
        275                 280                 285

Asp Leu Lys Pro Glu Asn Ile Leu Phe Val Asn Ser Asp Tyr Glu Leu
    290                 295                 300

Thr Tyr Asn Leu Glu Lys Lys Arg Asp Glu Arg Ser Val Lys Ser Thr
305                 310                 315                 320

Ala Val Arg Val Val Asp Phe Gly Ser Ala Thr Phe Asp His Glu His
                325                 330                 335

His Ser Thr Ile Val Ser Thr Arg His Tyr Arg Ala Pro Glu Val Ile
                340                 345                 350

Leu Glu Leu Gly Trp Ser Gln Pro Cys Asp Val Trp Ser Ile Gly Cys
        355                 360                 365

Ile Ile Phe Glu Tyr Tyr Val Gly Phe Thr Leu Phe Gln Thr His Asp
    370                 375                 380

Asn Arg Glu His Leu Ala Met Met Glu Arg Ile Leu Gly Pro Val Pro
385                 390                 395                 400

Ser Arg Met Ile Arg Lys Thr Arg Lys Gln Lys Tyr Phe Tyr Arg Gly
                405                 410                 415

Arg Leu Asp Trp Asp Glu Asn Thr Ser Ala Gly Arg Tyr Val Arg Glu
```

-continued

```
                  420                 425                 430
Asn Cys Lys Pro Leu Arg Arg Tyr Leu Thr Ser Glu Ala Glu Asp His
            435                 440                 445
His Gln Leu Phe Asp Leu Ile Glu Asn Met Leu Glu Tyr Glu Pro Ala
        450                 455                 460
Lys Arg Leu Thr Leu Gly Glu Ala Leu Gln His Pro Phe Phe Ala Cys
465                 470                 475                 480
Leu Arg Thr Glu Pro Pro Asn Thr Lys Leu Trp Asp Ser Ser Arg Asp
                485                 490                 495
Ile Ser Arg

<210> SEQ ID NO 10
<211> LENGTH: 490
<212> TYPE: PRT
<213> ORGANISM: Mus musculus

<400> SEQUENCE: 10

Met His His Cys Lys Arg Tyr Arg Ser Pro Glu Pro Asp Pro Tyr Leu
1               5                   10                  15
Thr Tyr Arg Trp Lys Arg Arg Ser Tyr Ser Arg Glu His Glu Gly
            20                  25                  30
Arg Leu Arg Tyr Pro Ser Arg Arg Glu Pro Pro Arg Arg Ser Arg
        35                  40                  45
Ser Arg Ser His Asp Arg Ile Pro Tyr Gln Arg Arg Tyr Arg Glu His
    50                  55                  60
Arg Asp Ser Asp Thr Tyr Arg Cys Glu Glu Arg Ser Pro Ser Phe Gly
65                  70                  75                  80
Glu Asp Cys Tyr Gly Ser Ser Arg Ser Arg His Arg Arg Arg Ser Arg
                85                  90                  95
Glu Arg Ala Pro Tyr Arg Thr Arg Lys His Ala His His Cys His Lys
            100                 105                 110
Arg Arg Thr Arg Ser Cys Ser Ser Ala Ser Ser Arg Ser Gln Gln Ser
        115                 120                 125
Ser Lys Arg Ser Ser Arg Ser Val Glu Asp Asp Lys Glu Gly His Leu
    130                 135                 140
Val Cys Arg Ile Gly Asp Trp Leu Gln Glu Arg Tyr Glu Ile Val Gly
145                 150                 155                 160
Asn Leu Gly Glu Gly Thr Phe Gly Lys Val Val Glu Cys Leu Asp His
                165                 170                 175
Ala Arg Gly Lys Ser Gln Val Ala Leu Lys Ile Ile Arg Asn Val Gly
            180                 185                 190
Lys Tyr Arg Glu Ala Ala Arg Leu Glu Ile Asn Val Leu Lys Lys Ile
        195                 200                 205
Lys Glu Lys Asp Lys Glu Asn Lys Phe Leu Cys Val Leu Met Ser Asp
    210                 215                 220
Trp Phe Asn Phe His Gly His Met Cys Ile Ala Phe Glu Leu Leu Gly
225                 230                 235                 240
Lys Asn Thr Phe Glu Phe Leu Lys Glu Asn Asn Phe Gln Pro Tyr Pro
                245                 250                 255
Leu Pro His Val Arg His Met Ala Tyr Gln Leu Cys His Ala Leu Arg
            260                 265                 270
Phe Leu His Glu Asn Gln Leu Thr His Thr Asp Leu Lys Pro Glu Asn
        275                 280                 285
Ile Leu Phe Val Asn Ser Glu Phe Glu Thr Leu Tyr Asn Glu His Lys
```

```
                    290                 295                 300
Ser Cys Glu Glu Lys Ser Val Lys Asn Thr Ser Ile Arg Val Ala Asp
305                 310                 315                 320

Phe Gly Ser Ala Thr Phe Asp His Glu His Thr Thr Ile Val Ala
                325                 330                 335

Thr Arg His Tyr Arg Pro Pro Glu Val Ile Leu Glu Leu Gly Trp Ala
            340                 345                 350

Gln Pro Cys Asp Val Trp Ser Ile Gly Cys Ile Leu Phe Glu Tyr Tyr
                355                 360                 365

Arg Gly Phe Thr Leu Phe Gln Thr His Glu Asn Arg Glu His Leu Val
            370                 375                 380

Met Met Glu Lys Ile Leu Gly Pro Ile Pro Ser His Met Ile His Arg
385                 390                 395                 400

Thr Arg Lys Gln Lys Tyr Phe Tyr Lys Gly Leu Val Trp Asp Glu
                405                 410                 415

Asn Ser Ser Asp Gly Arg Tyr Val Lys Glu Asn Cys Lys Pro Leu Lys
                420                 425                 430

Ser Tyr Met Leu Gln Asp Ser Leu Glu His Val Gln Leu Phe Asp Leu
            435                 440                 445

Met Arg Arg Met Leu Glu Phe Asp Pro Ala Gln Arg Ile Thr Leu Ala
    450                 455                 460

Glu Ala Leu Leu His Pro Phe Phe Ala Gly Leu Thr Pro Glu Glu Arg
465                 470                 475                 480

Ser Phe His Ser Ser Arg Asn Pro Ser Arg
                485                 490

<210> SEQ ID NO 11
<211> LENGTH: 481
<212> TYPE: PRT
<213> ORGANISM: Mus musculus

<400> SEQUENCE: 11

Met Arg His Ser Lys Arg Thr His Cys Pro Asp Trp Asp Ser Arg Glu
1               5                   10                  15

Ser Trp Gly His Glu Ser Tyr Ser Gly Ser His Lys Arg Lys Arg Arg
                20                  25                  30

Ser His Ser Ser Thr Gln Glu Asn Arg His Cys Lys Pro His His Gln
            35                  40                  45

Phe Lys Asp Ser Asp Cys His Tyr Leu Glu Ala Arg Cys Leu Asn Glu
    50                  55                  60

Arg Asp Tyr Arg Asp Arg Arg Tyr Ile Asp Glu Tyr Arg Asn Asp Tyr
65                  70                  75                  80

Cys Glu Gly Tyr Val Pro Arg His Tyr His Arg Asp Val Glu Ser Thr
                85                  90                  95

Tyr Arg Ile His Cys Ser Lys Ser Ser Val Arg Ser Arg Ser Ser
            100                 105                 110

Pro Lys Arg Lys Arg Asn Arg Pro Cys Ala Ser His Gln Ser His Ser
    115                 120                 125

Lys Ser His Arg Arg Lys Arg Ser Arg Ser Ile Glu Asp Asp Glu Glu
130                 135                 140

Gly His Leu Ile Cys Gln Ser Gly Asp Val Leu Arg Ala Arg Tyr Glu
145                 150                 155                 160

Ile Val Asp Thr Leu Gly Glu Gly Ala Phe Gly Lys Val Val Glu Cys
                165                 170                 175
```

```
Ile Asp His Gly Met Asp Gly Leu His Val Ala Val Lys Ile Val Lys
            180                 185                 190

Asn Val Gly Arg Tyr Arg Glu Ala Arg Ser Glu Ile Gln Val Leu
        195                 200                 205

Glu His Leu Asn Ser Thr Asp Pro Asn Ser Val Phe Arg Cys Val Gln
    210                 215                 220

Met Leu Glu Trp Phe Asp His His Gly His Val Cys Ile Val Phe Glu
225                 230                 235                 240

Leu Leu Gly Leu Ser Thr Tyr Asp Phe Ile Lys Glu Asn Ser Phe Leu
                245                 250                 255

Pro Phe Gln Ile Asp His Ile Arg Gln Met Ala Tyr Gln Ile Cys Gln
            260                 265                 270

Ser Ile Asn Phe Leu His His Asn Lys Leu Thr His Thr Asp Leu Lys
        275                 280                 285

Pro Glu Asn Ile Leu Phe Val Lys Ser Asp Tyr Val Val Lys Tyr Asn
    290                 295                 300

Ser Lys Met Lys Arg Asp Glu Arg Thr Leu Lys Asn Thr Asp Ile Lys
305                 310                 315                 320

Val Val Asp Phe Gly Ser Ala Thr Tyr Asp Asp Glu His His Ser Thr
                325                 330                 335

Leu Val Ser Thr Arg His Tyr Arg Ala Pro Glu Val Ile Leu Ala Leu
            340                 345                 350

Gly Trp Ser Gln Pro Cys Asp Val Trp Ser Ile Gly Cys Ile Leu Ile
        355                 360                 365

Glu Tyr Tyr Leu Gly Phe Thr Val Phe Gln Thr His Asp Ser Lys Glu
    370                 375                 380

His Leu Ala Met Met Glu Arg Ile Leu Gly Pro Ile Pro Ala His Met
385                 390                 395                 400

Ile Gln Lys Thr Arg Lys Arg Lys Tyr Phe His His Asn Gln Leu Asp
                405                 410                 415

Trp Asp Glu His Ser Ser Ala Gly Arg Tyr Val Arg Arg Arg Cys Lys
            420                 425                 430

Pro Leu Lys Glu Phe Met Leu Cys His Asp Glu His Glu Lys Leu
        435                 440                 445

Phe Asp Leu Val Arg Arg Met Leu Glu Tyr Asp Pro Ala Arg Arg Ile
    450                 455                 460

Thr Leu Asp Glu Ala Leu Gln His Pro Phe Phe Asp Leu Leu Lys Arg
465                 470                 475                 480

Lys

<210> SEQ ID NO 12
<211> LENGTH: 491
<212> TYPE: PRT
<213> ORGANISM: Xenopus lavis

<400> SEQUENCE: 12

Met Pro His Ser Arg Arg Tyr Gly Ser Ser Glu Arg Gly Ser Tyr Arg
1               5                   10                  15

Ser Arg Lys His Arg Arg Arg Ser Arg Ser Arg Ser Ser Ser
            20                  25                  30

Ser Ser Asp Arg Gly Arg Glu Arg His Met His Gly Asp Gly Tyr
        35                  40                  45

His Glu Arg Ser Arg Ser Tyr Glu Glu Arg Ser Ser Asp Arg Arg Ala
    50                  55                  60
```

```
Tyr Asp Arg Arg Tyr Cys Asp Ser Tyr Arg Arg Asn Asp Tyr Ser Arg
 65                  70                  75                  80

Asp Arg Gly Asp Val Tyr Tyr Glu Thr Asp Tyr Asp Tyr Lys His Ser
             85                  90                  95

Arg Asp Asp Ser Tyr Arg Ser Thr Arg Lys Gln Lys Arg Arg Asn
            100                 105                 110

Arg Arg Thr Arg Ser Tyr Ser Gln Ser Ser Arg Ser Arg Gln Ser
        115                 120                 125

Ser Arg Arg Ala Lys Ser Val Glu Asp Val Glu Gly His Leu Ile
    130                 135                 140

Tyr His Ser Gly Asp Trp Leu Gln Glu Arg Tyr Glu Ile Val Ser Thr
145                 150                 155                 160

Leu Gly Glu Gly Thr Phe Gly Arg Val Val Gln Cys Lys Asp His Arg
                165                 170                 175

Arg Gly Gly Ser Arg Val Ala Leu Lys Ile Ile Lys Asn Val Glu Lys
            180                 185                 190

Tyr Lys Glu Ala Ala Arg Leu Glu Ile Asn Val Leu Glu Lys Ile Asn
        195                 200                 205

Glu Lys Asp Pro Glu Asn Lys His Leu Cys Val Gln Met Phe Asp Trp
    210                 215                 220

Phe Asp Tyr His Gly His Met Cys Ile Ser Phe Glu Leu Leu Gly Leu
225                 230                 235                 240

Ser Thr Phe Asp Phe Leu Lys Glu Asn Asn Tyr Phe Pro Tyr Pro Ile
                245                 250                 255

His Gln Val Arg His Met Ala Leu Gln Leu Cys Gln Ala Met Lys Phe
            260                 265                 270

Leu His Asp Asn Lys Leu Thr His Thr Asp Leu Lys Pro Glu Asn Ile
        275                 280                 285

Leu Phe Val Ser Ser Asp Tyr Glu Leu Arg Tyr Asn Met Glu Lys Lys
    290                 295                 300

Arg Asp Glu Arg Cys Val Lys Ser Thr Asp Ile Arg Val Val Asp Phe
305                 310                 315                 320

Gly Ser Ala Thr Phe Asp His Glu His His Ser Thr Ile Val Ser Thr
                325                 330                 335

Arg His Tyr Arg Ala Pro Glu Val Leu Leu Glu Leu Gly Trp Asn Gln
            340                 345                 350

Pro Cys Asp Val Trp Ser Val Gly Cys Ile Ile Phe Glu Tyr Tyr Val
        355                 360                 365

Gly Phe Thr Leu Phe Gln Thr His Asp Asn Arg Glu His Leu Ala Met
    370                 375                 380

Met Glu Arg Ile Leu Gly Pro Ile Pro Ser Arg Met Ile Arg Lys Thr
385                 390                 395                 400

Arg Lys Gln Lys Tyr Phe Tyr His Gly Arg Leu Asp Trp Asp Asn
                405                 410                 415

Thr Ser Ala Gly Arg Tyr Val Arg Glu Asn Cys Lys Pro Leu Arg Arg
            420                 425                 430

Tyr Met Met Met Glu Thr Glu His His Gln Phe Phe Asn Leu Ile
        435                 440                 445

Glu Gly Leu Leu Gly Tyr Glu Pro Ser Lys Arg Met Thr Leu Ala Ala
    450                 455                 460

Ala Leu Lys His Pro Phe Phe Asn Pro Leu Lys Gly Asp Pro Thr Leu
465                 470                 475                 480

Lys His Trp Asp Thr Gly Arg Asp Ile Ser Arg
```

485        490

<210> SEQ ID NO 13
<211> LENGTH: 517
<212> TYPE: PRT
<213> ORGANISM: Drosophila melanogaster

<400> SEQUENCE: 13

Met Cys Val Arg Phe Gln Met Pro Arg Thr Arg Leu His His Ser
1               5                   10                  15

Arg Asp Arg Ser Ser Ala Gly Thr Arg Asp Lys Arg Arg Arg His Asp
            20                  25                  30

Thr Ala Asp His Ser Pro Pro Leu Ala Glu Ala Pro Ser Pro Pro Arg
        35                  40                  45

Ile Thr Asn Thr His His Thr Arg Ser Ala Ala Lys Arg Arg Arg His
    50                  55                  60

Glu Leu Asp Ala Lys Lys Ala Gln Ile Ser Lys Glu Pro Thr Phe Asp
65                  70                  75                  80

Asp Ser Ile Ser Thr Arg Arg Lys Glu Arg Ser Lys Arg Ser His
                85                  90                  95

Arg Lys Ser Pro Ala Ala Ser Arg Arg Gln His Lys Tyr Arg Tyr Arg
            100                 105                 110

Asp Glu Thr Ser His Ser Ser Ser Arg Arg Arg His Arg Asp Arg Ala
        115                 120                 125

Lys Asp Glu Arg Asp Ser Gly Arg Asn Asn Arg Gln Ser Gln Ala Lys
130                 135                 140

Thr Ala Lys Pro Val Ile Gln Asp Asp Ala Asp Gly His Leu Ile Tyr
145                 150                 155                 160

His Thr Gly Asp Ile Leu His His Arg Tyr Lys Ile Met Ala Thr Leu
                165                 170                 175

Gly Glu Gly Thr Phe Gly Arg Val Val Lys Val Lys Asp Met Glu Arg
            180                 185                 190

Asp Tyr Cys Met Ala Leu Lys Ile Ile Lys Asn Val Glu Lys Tyr Arg
        195                 200                 205

Glu Ala Ala Lys Leu Glu Ile Asn Ala Leu Glu Lys Ile Ala Gln Lys
210                 215                 220

Asp Pro His Cys Asp His Leu Cys Val Lys Met Ile Asp Trp Phe Asp
225                 230                 235                 240

Tyr His Gly His Met Cys Ile Val Phe Glu Met Leu Gly Leu Ser Val
                245                 250                 255

Phe Asp Phe Leu Arg Glu Asn Asn Tyr Glu Pro Tyr Pro Leu Asp Gln
            260                 265                 270

Val Arg His Met Ala Tyr Gln Leu Cys Tyr Ser Val Lys Phe Leu His
        275                 280                 285

Asp Asn Arg Leu Thr His Thr Asp Leu Lys Pro Glu Asn Ile Leu Phe
290                 295                 300

Val Asp Ser Asp Tyr Thr Ser His Tyr Asn His Lys Ile Asn Arg Glu
305                 310                 315                 320

Val Arg Arg Val Lys Asn Thr Asp Val Arg Leu Ile Asp Phe Gly Ser
                325                 330                 335

Ala Thr Phe Asp His Glu His His Ser Thr Ile Val Ser Thr Arg His
            340                 345                 350

Tyr Arg Ala Pro Glu Val Ile Leu Glu Leu Gly Trp Ser Gln Pro Cys
        355                 360                 365

|  |  |  |  |  |  |  |  |  |  |  |  |
|---|---|---|---|---|---|---|---|---|---|---|---|
| Asp | Val | Trp | Ser | Ile | Gly | Cys | Ile | Leu | Phe | Glu | Leu | Tyr | Leu | Gly | Ile |
|  | 370 |  |  |  | 375 |  |  |  | 380 |  |  |
| Thr | Leu | Phe | Gln | Thr | His | Asp | Asn | Arg | Glu | His | Leu | Ala | Met | Met | Glu |
| 385 |  |  |  |  | 390 |  |  |  |  | 395 |  |  |  |  | 400 |
| Arg | Ile | Leu | Gly | Gln | Ile | Pro | Tyr | Arg | Met | Ala | Arg | Lys | Thr | Lys | Thr |
|  |  |  |  | 405 |  |  |  |  | 410 |  |  |  |  | 415 |  |
| Lys | Tyr | Phe | Tyr | His | Gly | Lys | Leu | Asp | Trp | Asp | Glu | Lys | Ser | Ser | Ala |
|  |  |  | 420 |  |  |  |  | 425 |  |  |  |  | 430 |  |  |
| Gly | Arg | Tyr | Val | Arg | Asp | His | Cys | Lys | Pro | Leu | Phe | Leu | Cys | Gln | Leu |
|  |  | 435 |  |  |  |  | 440 |  |  |  |  | 445 |  |  |  |
| Ser | Asp | Ser | Glu | Asp | His | Cys | Glu | Leu | Phe | Ser | Leu | Ile | Lys | Lys | Met |
|  | 450 |  |  |  |  | 455 |  |  |  |  | 460 |  |  |  |  |
| Leu | Glu | Tyr | Glu | Pro | Ser | Ser | Arg | Ile | Thr | Leu | Gly | Glu | Ala | Leu | His |
| 465 |  |  |  |  | 470 |  |  |  |  | 475 |  |  |  |  | 480 |
| His | Pro | Phe | Phe | Asp | Arg | Leu | Pro | Pro | His | His | Arg | Val | Gly | Glu | Val |
|  |  |  |  | 485 |  |  |  |  | 490 |  |  |  |  | 495 |  |
| Ser | Asn | Lys | Gln | Pro | Leu | Ser | Ser | Gly | Ser | Ser | Ser | Arg | Glu | Arg | Ser |
|  |  |  | 500 |  |  |  |  | 505 |  |  |  |  | 510 |  |  |
| His | Ser | Leu | Ser | Arg |  |  |  |  |  |  |  |  |  |  |  |
|  |  |  | 515 |  |  |  |  |  |  |  |  |  |  |  |  |